(12) United States Patent
Fryman

(10) Patent No.: US 11,868,161 B2
(45) Date of Patent: *Jan. 9, 2024

(54) SYNCHRONIZED DISPLAY OF SCREEN CONTENT ON NETWORKED DEVICES

(71) Applicant: ICU Medical, Inc., San Clemente, CA (US)

(72) Inventor: Marshall E. Fryman, Lindenhurst, IL (US)

(73) Assignee: ICU Medical, Inc., San Clemente, CA (US)

( * ) Notice: Subject to any disclaimer, the term of this patent is extended or adjusted under 35 U.S.C. 154(b) by 180 days.

This patent is subject to a terminal disclaimer.

(21) Appl. No.: 17/302,501

(22) Filed: May 4, 2021

(65) Prior Publication Data

US 2021/0397396 A1  Dec. 23, 2021

Related U.S. Application Data

(63) Continuation of application No. 16/848,649, filed on Apr. 14, 2020, now Pat. No. 11,029,911, which is a
(Continued)

(51) Int. Cl.
*G06F 3/14* (2006.01)
*A61M 5/142* (2006.01)
(Continued)

(52) U.S. Cl.
CPC ........... *G06F 3/1423* (2013.01); *A61M 5/142* (2013.01); *A61M 5/1407* (2013.01);
(Continued)

(58) Field of Classification Search
CPC ...... G06F 3/1423; G06F 1/12; A61M 5/1407; A61M 5/1413; A61M 5/142;
(Continued)

(56) References Cited

U.S. PATENT DOCUMENTS 3,401,337 A   9/1968  Beusman et al.
3,484,681 A   12/1969  Grady, Jr. et al.
(Continued)

FOREIGN PATENT DOCUMENTS

AU    2013216679    9/2013
BR    PI0704229-9   11/2009
(Continued)

OTHER PUBLICATIONS

Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.
(Continued)

*Primary Examiner* — Abdullahi E Salad
(74) *Attorney, Agent, or Firm* — Knobbe, Martens, Olson & Bear LLP

(57) ABSTRACT

A system configured to synchronize the displays of multiple infusion pumps is provided. In some embodiments, the system includes a plurality of infusion pumps in communication with a server. An individual infusion pump synchronizes its internal clock by communicating with the server. Based on the synchronized internal clock, the infusion pump determines the current time, calculates a parameter based on the current time, and causes screen content corresponding to the calculated parameter to be displayed.

20 Claims, 7 Drawing Sheets

Related U.S. Application Data continuation of application No. 16/058,799, filed on Aug. 8, 2018, now Pat. No. 10,656,894, application No. 17/302,501 is a continuation of application No. 16/058,799, filed on Aug. 8, 2018, now Pat. No. 10,656,894, which is a continuation of application No. 15/861,204, filed on Jan. 3, 2018, now Pat. No. 10,089,055.

(60) Provisional application No. 62/610,742, filed on Dec. 27, 2017.

(51) Int. Cl.
| | | |
|---|---|---|
| *G06F 1/12* | (2006.01) | |
| *G16H 20/10* | (2018.01) | |
| *A61M 5/14* | (2006.01) | |
| *G09G 5/12* | (2006.01) | |
| *G16H 40/67* | (2018.01) | |
| *G16H 20/17* | (2018.01) | |
| H04L 67/12 | (2022.01) | |
| H04L 67/1095 | (2022.01) | |

(52) U.S. Cl.
CPC ............ *A61M 5/1413* (2013.01); *G06F 1/12* (2013.01); *G09G 5/12* (2013.01); *G16H 20/10* (2018.01); *G16H 20/17* (2018.01); *G16H 40/67* (2018.01); *A61M 2205/3584* (2013.01); *A61M 2205/50* (2013.01); *A61M 2205/502* (2013.01); *A61M 2205/52* (2013.01); *A61M 2205/6072* (2013.01); *G09G 2350/00* (2013.01); *G09G 2354/00* (2013.01); *G09G 2358/00* (2013.01); *G09G 2370/02* (2013.01); *G09G 2370/022* (2013.01); *G09G 2370/04* (2013.01); *G09G 2370/16* (2013.01); *G09G 2380/08* (2013.01); *H04L 67/1095* (2013.01); *H04L 67/12* (2013.01)

(58) Field of Classification Search
CPC ...... A61M 2205/3584; A61M 2205/50; A61M 2205/502; A61M 2205/52; A61M 2205/6072; G09G 5/12; G09G 2350/00; G09G 2354/00; G09G 2358/00; G09G 2370/02; G09G 2370/022; G09G 2370/04; G09G 2370/16; G09G 2380/08; G16H 20/10; G16H 20/17; G16H 40/67; H04L 67/1095; H04L 67/12
See application file for complete search history.

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,894,431 A | 7/1975 | Muston et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,057,228 A | 11/1977 | Völker et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |

(56) References Cited

U.S. PATENT DOCUMENTS

| | | |
|---|---|---|
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,515,584 A | 5/1985 | Abe et al. |
| 4,519,792 A | 5/1985 | Dawe |
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | Kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Blomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,769,001 A | 9/1988 | Prince |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,908,019 A | 3/1990 | Urquhart et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |

(56) References Cited

U.S. PATENT DOCUMENTS

| | | |
|---|---|---|
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,014,798 A | 5/1991 | Glynn |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,040,699 A | 8/1991 | Gangemi |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,260,665 A | 11/1993 | Goldberg |
| 5,257,206 A | 12/1993 | Hanson |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,304,216 A | 4/1994 | Wallace |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |

(56) References Cited

U.S. PATENT DOCUMENTS

| | | |
|---|---|---|
| 5,423,748 A | 6/1995 | Uhala |
| 5,423,749 A | 6/1995 | Merte et al. |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,685,866 A | 11/1997 | Lopez |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,734,464 A | 3/1998 | Gibbs |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |

(56) References Cited

U.S. PATENT DOCUMENTS

| | | |
|---|---|---|
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,028,412 A | 2/2000 | Shine et al. |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,336,053 B1 | 1/2002 | Beatty |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |

(56) References Cited

U.S. PATENT DOCUMENTS

| | | |
|---|---|---|
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,606,047 B1 | 8/2003 | Börjesson et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouda et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |

(56) References Cited

U.S. PATENT DOCUMENTS

| | | |
|---|---|---|
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,174,789 B2 | 2/2007 | Orr et al. |
| 7,185,288 B2 | 2/2007 | Mckeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Gimdt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| 7,338,470 B2 | 3/2008 | Katz |
| 7,347,836 B2 | 3/2008 | Peterson et al. |
| 7,347,854 B2 | 3/2008 | Shelton et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,477,997 B2 | 1/2009 | Kaplit |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,605,730 B2 | 10/2009 | Tomioka et al. |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenskow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de La Huerga |
| 7,945,452 B2 | 5/2011 | Fathallah et al. |
| 7,976,508 B2 | 7/2011 | Hoag |
| 7,981,073 B2 | 7/2011 | Mollstam |
| 7,981,082 B2 | 7/2011 | Wang et al. |
| 7,998,134 B2 | 8/2011 | Fangrow |
| 8,002,736 B2 | 8/2011 | Patrick et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,514 B2 | 12/2011 | Butterfield et al. |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blomquist |
| 8,175,668 B1 | 5/2012 | Nabutovsky et al. |
| 8,177,739 B2 | 5/2012 | Cartledge et al. |
| 8,180,440 B2 | 5/2012 | McCombie et al. |
| 8,185,322 B2 | 5/2012 | Schroeder et al. |
| 8,197,444 B1 | 6/2012 | Bazargan et al. |
| 8,219,413 B2 | 7/2012 | Martinez et al. |
| 8,221,395 B2 | 7/2012 | Shelton et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,409,164 B2 | 4/2013 | Fangrow |
| 8,449,524 B2 | 5/2013 | Braig et al. |
| 8,469,942 B2 | 6/2013 | Kow et al. |

(56) References Cited

U.S. PATENT DOCUMENTS

| | | |
|---|---|---|
| 8,477,307 B1 | 7/2013 | Yufa et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,522,832 B2 | 9/2013 | Lopez et al. |
| 8,523,797 B2 | 9/2013 | Lowery et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,728,020 B2 | 5/2014 | Caleffi et al. |
| 8,758,306 B2 | 6/2014 | Lopez et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,905,965 B2 | 12/2014 | Mandro et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |
| 9,190,010 B2 | 11/2015 | Vik et al. |
| 9,240,002 B2 | 1/2016 | Hume et al. |
| 9,272,089 B2 | 3/2016 | Jacobson et al. |
| 9,316,216 B1 | 4/2016 | Cook et al. |
| 9,333,291 B2 | 5/2016 | Jacobson et al. |
| 9,381,296 B2 | 7/2016 | Arrizza et al. |
| 9,393,362 B2 | 7/2016 | Cozmi et al. |
| 9,468,718 B2 | 10/2016 | Hung et al. |
| 9,498,583 B2 | 11/2016 | Sur et al. |
| 9,545,475 B2 | 1/2017 | Borges et al. |
| 9,707,341 B2 | 7/2017 | Dumas, III et al. |
| 9,764,087 B2 | 9/2017 | Peterfreund et al. |
| 9,852,265 B1 | 12/2017 | Treacy et al. |
| 9,883,987 B2 | 2/2018 | Lopez et al. |
| 9,943,269 B2 * | 4/2018 | Muhsin .............. A61B 5/14551 |
| 9,995,611 B2 | 6/2018 | Ruchti et al. |
| 10,022,498 B2 | 7/2018 | Ruchti et al. |
| 10,046,112 B2 | 8/2018 | Oruklu et al. |
| 10,089,055 B1 | 10/2018 | Fryman |
| 10,099,009 B1 | 10/2018 | Anderson et al. |
| 10,166,328 B2 | 1/2019 | Oruklu et al. |
| 10,342,917 B2 | 7/2019 | Shubinsky et al. |
| 10,430,761 B2 | 10/2019 | Hume et al. |
| 10,463,788 B2 | 11/2019 | Day |
| 10,549,248 B2 | 2/2020 | Brown et al. |
| 10,578,474 B2 | 3/2020 | Ruchti et al. |
| 10,596,316 B2 | 3/2020 | Dumas, III et al. |
| 10,635,784 B2 | 4/2020 | Rubalcaba, Jr. et al. |
| 10,656,894 B2 | 5/2020 | Fryman |
| 10,682,102 B2 | 6/2020 | Declerck |
| 10,709,885 B2 | 7/2020 | Janders et al. |
| 10,850,024 B2 | 12/2020 | Day et al. |
| 10,874,793 B2 | 12/2020 | Oruklu et al. |
| 11,004,035 B2 | 5/2021 | Hume et al. |
| D923,050 S | 6/2021 | Kataoka et al. |
| 11,029,911 B2 | 6/2021 | Fryman |
| D928,813 S | 8/2021 | Nurutdinov et al. |
| D928,840 S | 8/2021 | Amit et al. |
| 11,090,431 B2 | 8/2021 | Dumas, III et al. |
| D931,884 S | 9/2021 | Bryant et al. |
| 11,135,360 B1 | 10/2021 | Jacobson et al. |
| 11,246,985 B2 | 2/2022 | Gylland et al. |
| 11,298,456 B2 | 4/2022 | Shubinsky et al. |
| 11,324,888 B2 | 5/2022 | Shubinsky et al. |
| 11,344,668 B2 | 5/2022 | Sileika et al. |
| 11,344,673 B2 | 5/2022 | Lindo et al. |
| 11,376,361 B2 | 7/2022 | Ruchti et al. |
| 11,378,430 B2 | 7/2022 | Ruchti et al. |
| 11,395,875 B2 | 7/2022 | Rubalcaba, Jr. et al. |
| 11,433,177 B2 | 9/2022 | Oruklu et al. |
| 11,596,737 B2 | 3/2023 | Dumas, III et al. |
| 11,599,854 B2 | 3/2023 | Hume et al. |
| 11,623,042 B2 | 4/2023 | Day |
| 2001/0007636 A1 | 7/2001 | Butterfield |
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |
| 2002/0013545 A1 | 1/2002 | Soltanpour et al. |
| 2002/0013551 A1 | 1/2002 | Zaitsu et al. |
| 2002/0015018 A1 | 2/2002 | Shimazu et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0040208 A1 | 4/2002 | Flaherty et al. |
| 2002/0044059 A1 | 4/2002 | Reeder et al. |
| 2002/0045806 A1 | 4/2002 | Baker, Jr. et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0093641 A1 | 7/2002 | Ortyn et al. |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0168278 A1 | 11/2002 | Jeon et al. |
| 2002/0173703 A1 | 11/2002 | Lebel et al. |
| 2002/0183693 A1 | 12/2002 | Peterson et al. |
| 2003/0009244 A1 | 1/2003 | Engleson |
| 2003/0013959 A1 | 1/2003 | Grunwald et al. |
| 2003/0018289 A1 | 1/2003 | Ng et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158508 A1 | 8/2003 | DiGianfilippo |
| 2003/0160683 A1 | 8/2003 | Blomquist |
| 2003/0163789 A1 | 8/2003 | Blomquist |

(56) References Cited

U.S. PATENT DOCUMENTS

| | | |
|---|---|---|
| 2003/0173408 A1 | 9/2003 | Mosher, Jr. et al. |
| 2003/0186833 A1 | 10/2003 | Huff et al. |
| 2003/0187338 A1 | 10/2003 | Say et al. |
| 2003/0194328 A1 | 10/2003 | Bryant et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0216682 A1 | 11/2003 | Junker |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |
| 2004/0119753 A1 | 6/2004 | Zencke |
| 2004/0120825 A1 | 6/2004 | Bouton et al. |
| 2004/0128162 A1 | 7/2004 | Schlotterbeck et al. |
| 2004/0128163 A1 | 7/2004 | Goodman et al. |
| 2004/0133166 A1 | 7/2004 | Moberg et al. |
| 2004/0145114 A1 | 7/2004 | Ippolito et al. |
| 2004/0147034 A1 | 7/2004 | Gore et al. |
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172289 A1 | 9/2004 | Kozic et al. |
| 2004/0172301 A1 | 9/2004 | Mihai et al. |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0247445 A1 | 12/2004 | Nelson et al. |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0108057 A1 | 5/2005 | Cohen et al. |
| 2005/0119597 A1 | 6/2005 | O'Mahony et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0197649 A1 | 9/2005 | Shelton et al. |
| 2005/0204828 A1 | 9/2005 | Lee et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136095 A1 | 6/2006 | Rob et al. |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0180916 A1 | 8/2006 | Wyland |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229918 A1 | 10/2006 | Fotsch et al. |
| 2006/0235353 A1 | 10/2006 | Gelfand et al. |
| 2006/0255149 A1 | 11/2006 | Retter et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0265246 A1 | 11/2006 | Hoag |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060871 A1 | 3/2007 | Istoc |
| 2007/0060872 A1 | 3/2007 | Hall et al. |
| 2007/0060874 A1 | 3/2007 | Nesbitt et al. |

(56) References Cited

U.S. PATENT DOCUMENTS

| | | |
|---|---|---|
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084286 A1 | 4/2007 | Ajay et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0094045 A1 | 4/2007 | Cobbs et al. |
| 2007/0094046 A1 | 4/2007 | Cobbs et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0156456 A1 | 7/2007 | McGillin et al. |
| 2007/0179436 A1 | 8/2007 | Braig et al. |
| 2007/0179437 A1 | 8/2007 | Grage et al. |
| 2007/0180916 A1 | 8/2007 | Tian et al. |
| 2007/0191770 A1 | 8/2007 | Moberg et al. |
| 2007/0191817 A1 | 8/2007 | Martin |
| 2007/0197963 A1 | 8/2007 | Griffiths et al. |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0250339 A1 | 10/2007 | Mallett et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0077116 A1 | 3/2008 | Dailey et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0169044 A1 | 7/2008 | Osborne et al. |
| 2008/0172030 A1 | 7/2008 | Blomquist et al. |
| 2008/0177254 A1 | 7/2008 | Shelton et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1* | 3/2009 | Castellucci ............ H04L 12/14 709/229 |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0099866 A1 | 4/2009 | Newman |
| 2009/0105636 A1 | 4/2009 | Hayter et al. |
| 2009/0112155 A1 | 4/2009 | Zhao |
| 2009/0114037 A1 | 5/2009 | Smith |
| 2009/0119330 A1 | 5/2009 | Sampath et al. |
| 2009/0124963 A1 | 5/2009 | Hogard et al. |
| 2009/0124964 A1 | 5/2009 | Leach et al. |
| 2009/0126825 A1 | 5/2009 | Eliuk et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1* | 7/2009 | Roberts ................. G16H 40/67 607/60 |
| 2009/0177769 A1* | 7/2009 | Roberts ................. G16H 40/40 709/224 |
| 2009/0177992 A1 | 7/2009 | Rubalcaba et al. |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0198347 A1 | 8/2009 | Kirzinger |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2010/0022988 A1 | 1/2010 | Wochner |
| 2010/0280430 A1 | 1/2010 | Caleffi et al. |
| 2010/0036310 A1 | 2/2010 | Hillman |
| 2010/0056992 A1 | 3/2010 | Hayter |
| 2010/0057042 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |

(56) References Cited

U.S. PATENT DOCUMENTS

| | | |
|---|---|---|
| 2010/0212675 A1 | 8/2010 | Walling et al. |
| 2010/0217154 A1 | 8/2010 | Deshmukh et al. |
| 2010/0217621 A1 | 8/2010 | Schoenberg |
| 2010/0256562 A1 | 10/2010 | Cartledge et al. |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0312039 A1 | 12/2010 | Quirico et al. |
| 2010/0317093 A1 | 12/2010 | Turewicz et al. |
| 2010/0317952 A1 | 12/2010 | Budiman et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0040247 A1 | 2/2011 | Mandro et al. |
| 2011/0046558 A1 | 2/2011 | Gravesen et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0107251 A1 | 5/2011 | Guaitoli et al. |
| 2011/0137241 A1 | 6/2011 | DelCastillo et al. |
| 2011/0144595 A1 | 6/2011 | Cheng |
| 2011/0152770 A1 | 6/2011 | Diperna et al. |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0218514 A1 | 9/2011 | Rebours |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0313390 A1 | 12/2011 | Roy et al. |
| 2011/0319728 A1 | 12/2011 | Petisce et al. |
| 2011/0320049 A1 | 12/2011 | Chossat et al. |
| 2012/0025995 A1 | 2/2012 | Moberg et al. |
| 2012/0059234 A1 | 3/2012 | Barrett et al. |
| 2012/0068001 A1 | 3/2012 | Pushkarsky et al. |
| 2012/0083760 A1 | 4/2012 | Ledford et al. |
| 2012/0089411 A1 | 4/2012 | Srnka et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0222774 A1 | 9/2012 | Husnu et al. |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2012/0310204 A1 | 12/2012 | Krogh et al. |
| 2012/0323212 A1 | 12/2012 | Murphy |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0032634 A1 | 2/2013 | McKirdy |
| 2013/0041342 A1 | 2/2013 | Bernini et al. |
| 2013/0044111 A1 | 2/2013 | VanGilder et al. |
| 2013/0110538 A1 | 5/2013 | Butterfield et al. |
| 2013/0150766 A1 | 6/2013 | Olde et al. |
| 2013/0150821 A1 | 6/2013 | Bollish et al. |
| 2013/0184676 A1 | 7/2013 | Kamen et al. |
| 2013/0197930 A1 | 8/2013 | Garibaldi et al. |
| 2013/0201482 A1 | 8/2013 | Munro |
| 2013/0218080 A1 | 8/2013 | Peterfreund et al. |
| 2013/0116649 A1 | 9/2013 | Kouyoumjian et al. |
| 2013/0253430 A1 | 9/2013 | Kouyoumjian et al. |
| 2013/0253946 A1 | 9/2013 | Broselow |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1* | 11/2013 | Teng .................. G06F 3/1423 709/203 |
| 2013/0322201 A1 | 12/2013 | Hitchcock et al. |
| 2013/0345658 A1 | 12/2013 | Browne et al. |
| 2013/0345666 A1 | 12/2013 | Panduro et al. |
| 2014/0067425 A1 | 3/2014 | Dudar et al. |
| 2014/0145915 A1 | 5/2014 | Ribble et al. |
| 2014/0180711 A1 | 6/2014 | Kamen et al. |
| 2014/0224829 A1 | 8/2014 | Capone et al. |
| 2014/0267563 A1* | 9/2014 | Baca .................. H04N 21/237 348/14.08 |
| 2014/0303591 A1 | 10/2014 | Peterfreund et al. |
| 2014/0303754 A1 | 10/2014 | Nixon et al. |
| 2015/0025453 A1 | 1/2015 | Ledford et al. |
| 2015/0033073 A1* | 1/2015 | Yang .................. A61B 5/743 714/15 |
| 2015/0065988 A1 | 3/2015 | Holderle et al. |
| 2015/0168958 A1 | 6/2015 | Downie et al. |
| 2015/0224252 A1 | 8/2015 | Borges et al. |
| 2015/0265765 A1 | 9/2015 | Yavorsky et al. |
| 2015/0338340 A1 | 11/2015 | Jiang et al. |
| 2015/0343141 A1 | 12/2015 | Lindo et al. |
| 2015/0371004 A1 | 12/2015 | Jones |
| 2016/0042264 A1 | 2/2016 | Borges et al. |
| 2016/0110088 A1 | 4/2016 | Vik et al. |
| 2016/0144101 A1 | 5/2016 | Pananen |
| 2016/0151560 A1 | 6/2016 | Toro et al. |
| 2016/0151562 A1 | 6/2016 | Magers et al. |
| 2016/0151601 A1 | 6/2016 | Cardelius et al. |
| 2016/0158437 A1 | 6/2016 | Biasi et al. |
| 2016/0175517 A1 | 6/2016 | Sileika et al. |
| 2016/0193604 A1 | 7/2016 | McFarland et al. |
| 2016/0253460 A1 | 9/2016 | Kanada |
| 2016/0256622 A1 | 9/2016 | Day et al. |
| 2016/0339167 A1 | 11/2016 | Ledford et al. |
| 2017/0043089 A1* | 2/2017 | Handler ............... G16H 40/67 |
| 2017/0132867 A1 | 5/2017 | Berg et al. |
| 2017/0354941 A1 | 12/2017 | Brown et al. |
| 2018/0018440 A1 | 1/2018 | Sugawara |
| 2018/0028749 A1 | 2/2018 | Dumas, III et al. |
| 2018/0300994 A1 | 10/2018 | Nelson et al. |
| 2019/0091401 A1 | 3/2019 | Ruchti et al. |
| 2019/0101425 A1 | 4/2019 | Ruchti et al. |
| 2019/0117890 A1 | 4/2019 | Oruklu et al. |
| 2019/0196770 A1 | 6/2019 | Fryman |
| 2019/0262535 A1 | 8/2019 | Shubinsky et al. |
| 2019/0282757 A1 | 9/2019 | Gylland et al. |
| 2020/0069864 A1 | 3/2020 | Shubinsky et al. |
| 2020/0090122 A1 | 3/2020 | Hume |
| 2020/0113784 A1 | 4/2020 | Lopez et al. |
| 2020/0238007 A1 | 7/2020 | Day |
| 2020/0271499 A1 | 8/2020 | Ruchti et al. |
| 2020/0282137 A1 | 9/2020 | Dumas, III et al. |
| 2020/0324044 A1 | 10/2020 | Gylland et al. |
| 2020/0357500 A1 | 11/2020 | Rubalcaba, Jr. et al. |
| 2021/0170101 A1 | 6/2021 | Cavendish, Jr. et al. |
| 2021/0260283 A1 | 8/2021 | Oruklu et al. |
| 2022/0176037 A1 | 6/2022 | Jacobson et al. |
| 2022/0296806 A1 | 9/2022 | Shubinsky et al. |
| 2022/0305200 A1 | 9/2022 | Gylland et al. |
| 2022/0331518 A1 | 10/2022 | Shubinsky et al. |
| 2022/0362463 A1 | 11/2022 | Lindo et al. |
| 2023/0010290 A1 | 1/2023 | Oruklu et al. |
| 2023/0010638 A1 | 1/2023 | Rubalcaba, Jr. et al. |

(56) References Cited

U.S. PATENT DOCUMENTS

| | | | |
|---|---|---|---|
| 2023/0017117 A1 | 1/2023 | Sileika et al. | |
| 2023/0058662 A1 | 2/2023 | Ruchti et al. | |
| 2023/0058894 A1 | 2/2023 | Ruchti et al. | |

FOREIGN PATENT DOCUMENTS

| | | |
|---|---|---|
| CA | 2 113 473 | 3/1993 |
| CA | 2 551 817 | 7/2005 |
| CN | 107106042 | 8/2017 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 1 490 131 | 12/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2009-148592 | 7/2009 |
| JP | 2010-063767 | 3/2010 |
| JP | 5716879 | 3/2015 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |

(56) References Cited

FOREIGN PATENT DOCUMENTS

| | | |
|---|---|---|
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/036854 | 3/2013 |
| WO | WO 2013/096769 | 6/2013 |
| WO | WO 2015/134478 | 9/2015 |
| WO | WO 2017/051271 | 3/2017 |
| WO | WO 2017/144366 | 8/2017 |
| WO | WO 2017/197024 | 11/2017 |
| WO | WO 2017/214441 | 12/2017 |
| WO | WO 2019/092680 | 5/2019 |
| WO | WO 2020/214717 | 10/2020 |
| WO | WO 2021/113259 | 6/2021 |
| WO | WO 2022/020184 | 1/2022 |
| WO | WO 2022/125471 | 6/2022 |
| WO | WO 2023/064662 | 4/2023 |

OTHER PUBLICATIONS

ALARIS® Medical Systems, "Signature Edition® GOLD—Single & Dual Channel Infusion System", San Diego, CA, USA, date unknown, but believed to be at least as early as Nov. 29, 2008, pp. 2-88 & 2-91.
Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. <http://web.archive.org/web/20160403140025/http://www.baxter.com/news-media/newsroom/press-releases/2014/05_08_14_sigma.page>.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Buhrdorf et al., "Capacitive Micromachined Ultrasonic Transducers and their Application", Proceedings of the IEEE Ultrasonics Symposium, Feb. 2001, vol. 2, pp. 933-940.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, <https://store.cerner.com/items/7>.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", <https://web.archive.org/web/20090813092423/http://www.diffen.com/difference/Continually_vs_Continuously>, as accessed Aug. 13, 2009 in 4 pages.
"CritiCore® Monitor: Critical Fluid Output and Core Bladder Temperature Monitor", BARD Urological Catheter Systems, Advertisement, 2005, pp. 2.
Daimiwal et al., "Wireless Transfusion Supervision and Analysis Using Embedded System", IEEE, 2010 International Conference ICBBT, China, Apr. 2010, pp. 56-60.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. <http://archive.epo.org/epo/pubs/oj013/11_13/11_5033.pdf>.
"Decision of the Administrative Council of Oct. 27, 2009 Amending the Implementing Regulations to the European Patent Convention (CA/D 20/09)", Official Journal EPO Dec. 2009, Dec. 2009, pp. 582-584. <http://archive.epo.org/epo/pubs/oj009/12_09/12_5829.pdf>.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
"Froth", <http://www.merriam-webster.com/dictionary/froth>, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. <www.hospira.com/products_and_services/infusion_pumps/plum/index>.
Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
International Search Report and Written Opinion received in PCT Application No. PCT Application No. PCT/US2018/066913, dated Mar. 8, 2019 in 15 pages.

(56) References Cited

OTHER PUBLICATIONS

JMS Co., Ltd., "Infusion Pump: OT-701", Tokyo, Japan, 2002, pp. 4.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.
Kutcher et al., "The Effect of Lighting Conditions on Caries Interpretation with a Laptop Computer in a Clinical Setting", Elsevier, Oct. 2006, vol. 102, No. 4, pp. 537-543.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", <https://www.elektronik.ropla.eu/pdf/stock/mcp/mta11200b.pdf>, 1995, pp. 44.
Moghissi, Etie, MD, FACP, FACE, "Hyperglycemia in Hospitalized Patients", A Supplement to ACP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, <http://staff.ustc.edu.cn/~ketang/papers/TangSuganYaoQin_PR04.pdf>.
Thomas et al., "Implementation of a Tight Glycaemic Control Protocol Using a Web-Based Insulin Dose Calculator", Anaesthesia, 2005, vol. 60, pp. 1093-1100.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
International Preliminary Report on Patentability and Written Opinion received in PCT Application No. PCT/US2018/066913, dated Jul. 9, 2020 in 8 pages.
Abbott Laboratories, "LifeCare® 5000, Plum®: Concurrent Flow Infusion System with DataPort™", System Operating Manual, Version 1.6, Jul. 1998, pp. 76.

* cited by examiner

SYNCHRONIZED DISPLAY OF SCREEN CONTENT ON NETWORKED DEVICES

INCORPORATION BY REFERENCE TO ANY PRIORITY APPLICATIONS

This application is a continuation of U.S. application Ser. No. 16/848,649, filed Apr. 14, 2020, which is a continuation of U.S. application Ser. No. 16/058,799, filed Aug. 8, 2018, which is a continuation of U.S. application Ser. No. 15/861,204, filed Jan. 3, 2018, which claims priority to U.S. Provisional Application No. 62/610,742, filed on Dec. 27, 2017. Any and all applications for which a foreign or domestic priority claim is identified in the Application Data Sheet as filed with the present application are hereby incorporated herein by reference in their entirety under 37 CFR 1.57.

TECHNICAL FIELD

This disclosure relates to the field of networked devices, and particularly to techniques for synchronizing the screen content displayed on a plurality of networked devices.

BACKGROUND

Networked devices capable of displaying information are commonplace in modern network environments. Such networked devices may each include a display screen configured to display information generated by the networked device such as a status of the networked device, an error encountered by the networked device, etc. Based on the information displayed on the display screens, users may determine whether any action needs to be taken with respect to the networked devices.

SUMMARY

Various techniques for providing a synchronized display of screen content on a plurality of networked devices are described herein. Although many of the examples are described in the context of a hospital environment, the techniques described herein can be applied to any network environment including multiple networked devices. The networked devices described herein may include infusion pumps, other medical devices, or non-medical devices, or any combination thereof. The screen content described herein may be drug delivery metrics, other medical device screen content, other display screen content, or any combination thereof. The synchronization of the screen content displayed on multiple networked devices may be performed without having a centralized server communicate with each networked device to coordinate the content and/or timing of the displayed screen content. In some cases, synchronization of the screen content displayed on multiple networked devices is performed based on synchronizing the internal clocks of the respective networked devices with a reference time. In other cases, synchronization of the screen content displayed on multiple networked devices occurs without synchronizing the internal clocks of the respective networked devices and without utilizing a centralized server to synchronize the displays of the multiple networked devices. These and other embodiments are described in greater detail below with reference to FIGS. 1-7.

BRIEF DESCRIPTION OF THE DRAWINGS

The embodiments described herein are illustrated by way of example, and not by way of limitation, in the figures of the accompanying drawings in which like references indicate similar elements.

DETAILED DESCRIPTION

Introduction

Figure 1:
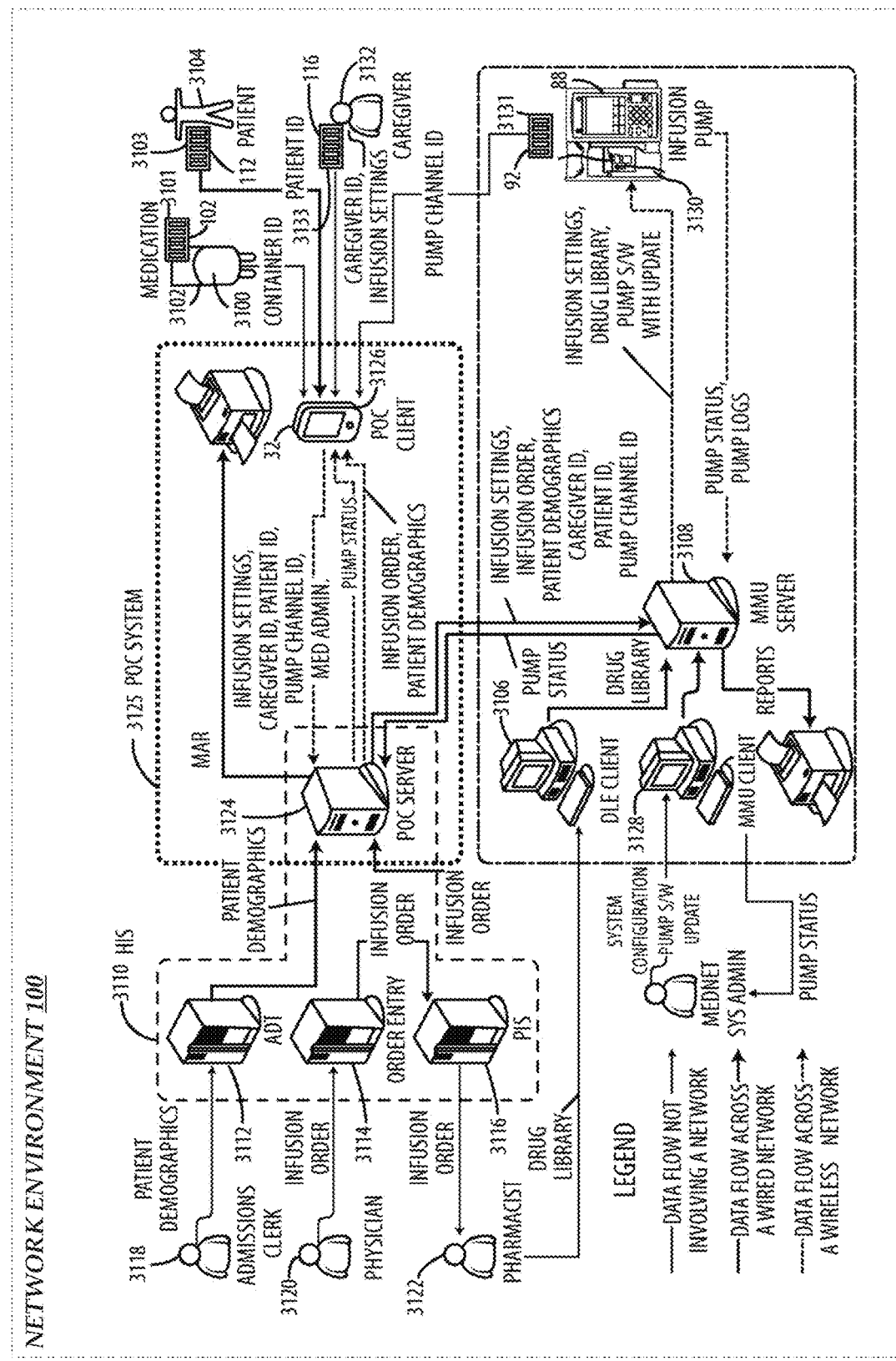
FIG. 1 is a schematic diagram of an example network environment including one or more networked devices in accordance with aspects of this disclosure.

A network environment may include multiple electronic devices. One example of such an environment is a hospital network environment, where a centralized server communicates with multiple medical devices such as patient care monitors and infusion pumps. In the hospital network environment, the centralized server may control how the medical devices in the hospital network environment operate and what kind of information is presented via the medical devices. For example, several patients may share a single room in a hospital, and the patients may each be assisted by a number of medical devices. Such medical devices may each include a display screen through which various physiological metrics, warnings, measurements, and other information may be presented to the caregiver or patient.

As the number of such networked devices displaying and updating screen content increases, viewing and understanding the displayed information becomes more difficult. For example, a caregiver may wish to quickly scan an array of 10 infusion pumps to determine whether the infusion pumps are functioning properly, infusing the medications at the correct rate, how much time it will be until the medication delivery is complete, etc. However, if the 10 infusion pumps are each cycling through multiple metrics on their displays (e.g., rate, dose, time remaining, volume infused, volume to be infused, etc.) at different times, the caregiver may find that distracting and inefficient. As another example, a system administrator may wish to scan an array of monitors to ensure that all of the servers are performing properly. However, if the monitors are cycling through different server statistics out of sync, it may be difficult for the system administrator to gather the necessary information from the monitors. Thus, an improved method of synchronizing the displays of such networked devices is desired.

Synchronizing Screen Content Displayed on Networked Devices

In some implementations, the networked devices described above (e.g., infusion pumps, monitors, etc.) in a network environment cause their respective screen content to be changed in response to a signal received from a server. For example, the server may transmit a "heartbeat" signal to each networked device every 15 seconds, indicating that the networked device should change the displayed content or switch to the next content in a given display order. Such a signal from the server may also indicate which content the networked device should display (e.g., by including a content identifier in the signal transmitted to the networked device). In such implementations, the signal would be received and processed by the individual networked devices at approximately the same time, and the content displayed on their displays would be synchronized as a result.

However, such use of heartbeat signals can consume valuable network resources (e.g., bandwidth) and overwhelm the network, especially if the network includes a large number of such networked devices. Further, processing such heartbeat signals from the server may require a sophisticated processor on the networked device and/or consume valuable processing power. In view of these technical considerations, in some cases, it may be beneficial to display and cycle through screen content without relying on such a heartbeat signal. In another implementation, the screen content may be displayed based on an internal clock maintained by the individual networked devices and without communicating with the server each time new screen content needs to be displayed. In such implementations, the amount of data transmitted across the network environment may be significantly reduced and valuable network resources and/or processing power can be preserved for other uses. The techniques for synchronizing the screen content displayed on networked devices in this manner are described in greater detail below with reference to FIGS. 2-7.

In yet another implementation, the individual networked devices locally store a fixed schedule of which metric to display at what time. In such an implementation, a networked device may store a table that specifies, for each controlling variable (e.g., clinical care area of an infusion pump), which metric should be displayed at a given time of day. For example, the table may specify that for networked devices in the intensive care unit should display metric #1 for the first 10 minutes of every hour, metric #2 for the second 10 minutes, metric #3 for the third 10 minutes, and so on, and for networked devices in the operating room should display metric #3 for the first 30 minutes of every hour, and metric #4 for the second 30 minutes of every hour. As another example, the table may specify, for each 5-second interval in the 24 hours of a given date, the metric to be displayed for the 5-second interval. However, locally storing such a table would consume a large amount of memory or disk space, which may not be desired for networked devices having limited memory/storage. Further, even if such a table is accessed from a remote network location, accessing the table over the network can consume valuable network resources (e.g., bandwidth) and overwhelm the network, especially if the network includes a large number of such networked devices. As discussed above, displaying the screen content based on an internal clock maintained by the individual networked devices and without storing or accessing large amounts of data specifying the screen content to be displayed at any given interval may provide certain technical benefits such as reducing the amount of storage space needed and/or data transmitted across the network environment and allowing valuable storage/network resources to be preserved for other uses.

With reference to FIG. 1, an example network environment in which one or more of the display synchronization techniques of the present disclosure may be utilized is described. Following the discussion of FIG. 1, specific details of the various embodiments of the present disclosure are described with reference to FIGS. 2-7.

Overview of Example Network Environment

FIG. 1 illustrates one embodiment of a system for administering medication via an infusion pump in a network environment 100. The medication management system (MMS) shown in FIG. 1 includes a medication management unit (MMU) server 3108 and a medical device, such as infusion pump 3130, operating in conjunction with one or more information systems or components of a hospital environment.

Intravenous (IV) fluid(s) and/or medication(s) 3100 in containers 3102 may be administered to a patient 3104 using the system shown in FIG. 1. Although the system shown in FIG. 1 utilizes barcodes and a barcode reader as apparatus to input and read machine-readable information, those skilled in the art will appreciate that other apparatus for reading or inputting information may be utilized. Moreover, a point of care (POC) client 3126 may include an identification receiver 32 adapted to recognize such indicia that may be provided in the MMS.

In certain aspects, the IV fluids and/or medications 3100 in container 3102 may be provided with new or supplemental labels with a unique infusion order identifying barcode by a pharmacist according to certain hospital practices. Specifically, drug container specific identification information, such as barcoded information on the container 3102 may include patient identification information, medication identification information, universal identification information, medical device delivery information, and/or medication order information. The IV fluids and/or medications 3100 in barcode-identified containers 3102 may be supplied to hospitals by various vendors, with preexisting unique barcode identifiers, which include medication information and other information, such as a National Disease Center (NDC) code, expiration information, drug interaction information, and the like.

In some aspects of the disclosure, the universal identification information on the container 3102 may be a unique medication order identifier that, by itself, identifies the order associated with the container. In other aspects, the identification information on the container 3102 may be a composite patient/order code that contains both a patient ID (such as a medical record number) and an order ID unique only within the context of the patient. In certain aspects, the identification information on the container 3102 may include a medication ID. The system identified in FIG. 1 may include a drug library editor (DLE) client 3106, such as a notebook, desktop or server computer. The DLE client 3106 may include DLE software. As described above, the MMU server 3108 may have MMU software that is installed and runs on the MMU server 3108. The drug library and other databases may be stored on the MMU server 3108, on a separate server, and/or in remote locations.

Hospital information systems (HIS) 3110 may include one or more computers connected by cabling, interfaces, and/or Ethernet connections. Alternatively, wireless connections and communications may be used in whole or in part. Servers provide processing capability and memory for storage of data and various application programs or modules, including but not limited to an admissions-discharge-and-transfer (ADT) module or computer 3112, a computerized physician order entry (CPOE) module or computer 3114, and a pharmacy information system (PIS) module or computer 3116. Hospital personnel, such as admission clerks 3118, physicians 3120, and pharmacists 3122, respectively, may be authorized to access these modules through client workstations connected to the servers in order to enter data, access information, run reports, and complete other tasks.

In the embodiment shown in FIG. 1, the HIS 3110 may also include a POC system 3125 including a server or POC computer 3124 (sometimes referred to as a barcode point of care server or computer), or the POC computer 3124 may be separate from the HIS 3110. The POC computer 3124 may act as a part of the POC system 3125 (sometimes referred to as the barcode point of care system or BPOC) and may be able to wirelessly communicate through a plurality of wireless communication nodes located throughout the hospital, utilizing a wireless communications protocol, such as IEEE 801.11, IEEE 802.11, or Bluetooth. The POC computer 3124 may communicate wirelessly with a portable thick client, POC client 3126, carried by a caregiver. The POC client 3126 may be a personal digital assistant (PDA) that includes significant memory, display, and processing capabilities. The POC client device may execute a variety of programs stored in its memory in some degree independently of the POC computer 3124.

In one embodiment of FIG. 1, the MMU server 3108 may be hard-wired to the DLE client 3106 and to a MMU client 3128. Alternatively, the MMU and DLE client functions may be combined onto a single client computer/workstation or may reside together with the MMU server 3108 on a single combined MMU/DLE server. The MMU server 3108 may reside in a location remote from the patient's room or treatment area. For instance, the MMU server 3108 may reside in a secure, climate controlled information technology room with other hospital servers, and computer equipment and its client terminals may be located in the pharmacy, biomedical engineering area, nurse station, or ward monitoring area. One MMU server 3108 may monitor, coordinate, and communicate with many infusion pumps 3130. For example, in one embodiment, the MMU software running on the MMU server 3108 may support up to one thousand infusion pumps concurrently.

In embodiment of FIG. 1, the POC client 3126 in the POC system 3125 may communicate through the POC server 3124 with the MMU server 3108. The MMU server 3108 may interface or communicate wirelessly with the infusion pump 3130 through the same wireless nodes utilized by the POC system 3125 and a connectivity engine and antenna on or in the infusion pump 3130. Communication between the infusion pump 3130 and the POC client 3126 may take place through the MMU server 3108 and POC server 3124. The MMU server 3108 may store in an associated memory both the logical ID and the network ID or Internet Protocol (IP) address of the infusion pump(s) 3130, such that only the MMU server 3108 may communicate in a direct wireless manner with the infusion pump 3130. Alternatively, the MMU server 3108 may provide the IP address and other information about the infusion pump 3130 to the POC system 3125 to facilitate direct communication between the POC system 3125 and the infusion pump 3130.

Upon admission to the hospital, the admission clerk 3118 or similar personnel may enter demographic information about each patient 3104 into an associated memory of the ADT module or computer 3112 of an HIS database stored in an associated memory of the HIS 3110. Each patient 3104 may be issued a patient identification wristband, bracelet, or tag 112 that may include an identifier 3103, such as a barcode or RFID tag, identifying the patient. The wristband, bracelet, or tag 112 may also include other information, in machine readable or human-readable form, such as the name of the patient's doctor, blood type, allergies, and the like.

The patient's doctor 3120 may prescribe medical treatment by entering a medication order into the CPOE module or computer 3114 within the HIS 3110. The medication order may specify a start time, stop time, a range of allowable doses, physiological targets, route, and site of administration. In the case of an order for infusion of fluids or medication, the order may be written in various formats, and may include the patient's name, patient ID number, a unique medication order or prescription number, a medication name, medication concentration, a dose or dosage, frequency, and/or a time of desired delivery. This information may be entered into the memory of the CPOE module or computer 3114, and may be stored in a memory associated with at least the POC server 3124.

The medication order may also be delivered electronically to the PIS module or computer 3116 in the pharmacy and may be stored in an associated memory. The pharmacist 3122 may screen the prescribed order, translate it into an order for dispensing medication, and prepare the medication or fluids with the proper additives and/or necessary diluents. The pharmacist 3122 may prepare and affix a label 102 with drug container specific identifying information 3101 to the medication or drug container 3102. The label may include in machine-readable and/or human-readable form medical device specific delivery information including but not limited to the dispense ID number, patient ID, drug name, drug concentration, container volume, volume-to-be-infused ("VTBI"), rate, duration, and the like. Only two of the three variables VTBI, rate, and duration may be defined as the third may be calculated when the other two are known. The labeled medication may be delivered to a secure, designated staging location or mobile drug cart on the ward or floor near the patient's room or treatment area. The medication order pending dispensing or administration may be posted to a task list in the HIS 3110 and POC system 3125 and stored in an associated memory.

The caregiver 3132 (e.g., a nurse) may use the identification receiver 32 associated with the POC client 3126 to scan the caregiver specific identification information 3133 or barcode on his/her caregiver identification badge 116 and enter a password, which logs the caregiver into the system and authorizes the caregiver to access a nurse's task list from the POC system 3125 through the POC client 3126. The caregiver 3132 may view from the task list that IV drugs are to be administered to certain patients 3104 in certain rooms. The caregiver 3132 obtains the necessary supplies, including medications, from the pharmacy and/or a staging area in the vicinity of the patient's room.

The caregiver 3132 may take the supplies to a patient's bedside, turn on the infusion pump 3130, verify that the network connection icon on the infusion pump 3130 indicates a network connection (for example, a wireless connection such as Wi-Fi or the like) is present, select the appropriate clinical care area (CCA) on the infusion pump 3130, and mount the IV bag, container, or vial 3102 and any associated tube set as required in position relative to the patient 3104 and infusion pump 3130 for infusion. Another connection icon on the infusion pump 3130 or pump user interface screen can indicate that a wired or wireless connection to the MMU server 3108 is present. Using the identification receiver/reader integral to the POC client 3126, the caregiver 3132 may scan the barcode on the patient's identification wristband, bracelet, or tag 112 or other patient identification device. A task list associated with that particular patient may appear on the POC client 3126 screen. The task list, which may also include orders to give other forms of treatment or medication by other routes (oral, topical, etc.), may be obtained from the HIS 3110 via the POC server 3124 and communicated wirelessly to the POC client 3126. In one embodiment, the list is generated by matching the scanned patient ID with the patient ID for orders in memory within the POC server 3124. In another embodiment, the order information may be obtained by scanning the drug container specific identification information for associated orders in memory within the POC server 3124, through the following step(s).

The caregiver 3132 may scan the medication barcode label 102 containing medication container specific identification information 3101 on the medication container 3102 with the POC client 3126. The POC client 3126 may highlight the IV administration task on the task list and send the scanned medication container specific identification information, such as dispense ID information, from the medication container 3102, to the POC server 3124. The POC server may use the medication container specific identification information to pull together the rest of the order details and send them back to the POC client 3126. The POC client 3126 may then display an IV Documentation Form on its screen. One side of the IV Documentation Form screen may show the order details as "ordered" and the other side may be reserved for a status report from the infusion pump 3130. The status report from the infusion pump 3130 may be transmitted to the POC client 3126 through the POC server 3124 and MMU server 3108. The lower portion of the IV Documentation Form screen may provide the caregiver 3132 with instructions (like to scan the infusion pump 3130 barcode) or identify whether the pump is running or stopped.

The caregiver 3132 may then scan the barcode label 92 associated with the infusion pump 3130 (or pump channel if the pump is a multi-channel pump). The barcode label 92 may contain medical device specific identification information 3131, such as the logical name and/or logical address of the device or channel. The POC system 3125 then automatically bundles the information into a program pump request containing the "order details" and in one embodiment, without further interaction with the caregiver 3132, transmits this information to the MMU server 3108.

The program pump request may include at least some of the following information (in HIS/POC system format): a Transaction ID, which may include a Logical Pump ID, a Pump Compartment, a Pump Channel ID, a Reference Device Address, a Caregiver ID, a Caregiver Name, a Patient/Person ID (HIS identifier), a Patient Name, a Patient Birth Date & Time, a Patient Gender, a Patient Weight, a Patient Height, and an Encounter ID which may include a Room, a Bed, and a Building (including CCA). The program pump request may also include Order Information or "order details", including an Order ID, a Start Date/Time, a Stop Date/Time, a Route of Administration, a Rate, a Duration of Infusion (Infuse Over), a Total Volume to be Infused (VTBI), an Ad Hoc Order Indicator, and Ingredients including HIS Drug Name or HIS Generic Drug Name, HIS Drug Identifier or HIS Generic Drug ID, Rx Type (Additive or Base), Strength w/units, and Volume w/units. The program pump request may further include Patient Controlled Analgesia (PCA) Orders Only information, such a PCA Mode-PCA only, Continuous only, or PCA and Continuous, a Lockout Interval (in minutes), a PCA Continuous Rate, a PCA Dose, a Loading Dose, a Dose Limit, a Dose Limit Time w/units, a Total Volume in vial or syringe, and Order Comments.

The MMU server 3108 may map or convert the wide range of expressions of units allowed by the HIS 3110 or POC system 3125 for POC client 3126 requests into the much more limited set of units allowed in the MMU server 3108 and infusion pump 3130. For example, the POC client 3126 request may express "g, gm, gram, or grams" whereas the MMU server 3108 and/or infusion pump 3130 may accept "grams" only. Infusion pump 3130 delivery parameters or infusion pump 3130 settings are mapped or converted from corresponding order information or "order details" of the program pump request.

The MMU server 3108 may store in an associated memory a mapping or translation table that keep track of the logical ID, serial number or other identifier of an infusion pump 3130 and the corresponding current network (static or dynamic) address (Internet Protocol (IP) address) or ID of the infusion pump 3130 on the network, which in this example is a wireless network. The MMU server 3108 may be able to translate or associate a given identifier of the infusion pump 3130 with its network address in the translation table and provide the network IP address to the requesting POC system 3125 or device. The MMU server 3108 may also store in an associated memory and/or look up the drug library applicable to the scanned infusion pump 3130 and/or convert the Drug ID and Strength from the pump program request into an index number of the medication at the desired strength or concentration from the drug library. The duration of the infusion may come from the POC system 3125 in hours and minutes and may be converted to just minutes for the infusion pump 3130 to recognize it. Volume or VTBI may be rounded to provide a value-specific and infuser-specific number of digits to the right of the decimal point. Units (of drug) may be converted to million units where appropriate. Patient weight may be converted and either rounded according to infuser-specific rules or not sent to the infuser.

Once the MMU server 3108 transforms the information from the program pump request into infusion pump settings or delivery parameters and other information in a format acceptable to the infusion pump 3130, the MMU server 3108 may wirelessly download a command message to the infusion pump 3130. If the infusion pump 3130 is not already equipped with the latest appropriate version of the hospital-established drug library, the MMU server 3108 may also automatically download a drug library to the infusion pump 3130. The hospital-established drug library may be maintained in a separate process undertaken by the biomedical engineer or pharmacist 3122 to place limits on the programming of the infusion pump 3130, as well as other infusion pump operating parameters such as default alarm settings for air in the line, occlusion pressure, and the like. The drug library may set up acceptable ranges or hard and/or soft limits for various drug delivery parameters in the infusion pump 3130.

The MMU server 3108 may also download to the infusion pump new versions, patches, or software updates of the infusion pump's internal operating system software. The infusion settings or delivery parameters and other information from the MMU server 3108 may be entered into the memory of the infusion pump 3130 and the infusion pump 3130 settings may automatically populate the programming screen(s) of the infusion pump 3130, just as if the caregiver 3132 had entered the information and settings manually. The infusion pump 3130 screen may populate with the name of the drug and drug concentration based on the drug library index number, patient weight, rate, VTBI, and/or duration. Further, the MMU server 3108 may transmit one or more synchronization signals or screen content display rules/parameters to the infusion pump 3130, as described in greater detail below with reference to FIGS. 2-7. A return message of confirmation signal may be sent to the MMU server 3108 by the infusion pump 3130 to indicate that the command message has been received. At this point, if necessary, the caregiver 3132 may manually enter any additional infusion settings or optional information that was not included in the command message.

The infusion pump 3130 may then prompt the caregiver 3132 to start the infusion pump 3130 by pressing the start button. When the caregiver 3132 presses the start button, a confirmation screen with the infusion settings programmed may be presented for confirmation and an auto-program acknowledgment message can be sent to the MMU server 3108 to forward without request (i.e., pushed in a near real-time manner) or provide to the POC system 3125 when requested or polled. When the caregiver 3132 presses the button to confirm, the infusion pump 3130 may begin delivering fluid according to the programmed settings. The infusion pump 3130 may send a status message to the MMU server 3108 indicating that the infusion pump 3130 was successfully auto-programmed, confirmed and started by the caregiver 3132, and is now delivering fluid. This information may also be displayed at the infusion pump. The MMU server 3108 may continue to receive logs and status messages wirelessly from the infusion pump 3130 periodically as the infusion progresses or when alarms occur.

The MMU server 3108 may report a portion of the initial status message to the POC client 3126 through the POC server 3124 (in MMU format) to indicate that the infusion pump 3130 has been auto-programmed and the caregiver 3132 has confirmed the settings. The MMU server 3108 may communicate to the POC system 3125 and/or at the infusion pump 3130 the actual Rate, VTBI, and Duration. A notation at the bottom of the screen of the POC client and/or the infusion pump may indicate that the infusion pump 3130 is running. The infusion pump 3130 may compare and give a visual, audio, or other type of affirmative signal if the pump information matches or acceptably corresponds with the ordered information. An initial determination of whether the pump information matches the order may be done in the MMU server 3108 and communicated to the POC client 3126 through the POC server 3124. Alternatively, the POC server 3124 or the infusion pump 3130 may make the necessary comparisons. If the pump information does not match the order, the infusion pump 3130 at the display 88 may output a visual, audio, or other type of negative signal, which may include an error message.

The caregiver 3132 may be prompted to review and press a save button on the infusion pump 3130 if the order has been begun as desired or any variations are acceptable. The MMU server 3108 may receive status, event, differences, and variation information from the infusion pump 3130 and pass such information to the POC system 3125. In a separate subsequent step, the nurse may electronically sign the record and presses a send button on the POC client 3126 to send the information to the patient's electronic medication record (EMR) or medication administration record (MAR).

Other Environments

FIG. 1 illustrates one example environment in which the various display synchronization techniques of the present disclosure may be utilized. However, the embodiments described herein are not limited to such an environment, and may be applied to any network environment including one or more networked devices having a display. An example system that may be implemented in one or more of such network environments to provide synchronized display of screen content is described below with reference to FIG. 2.

System Overview

Figure 2:
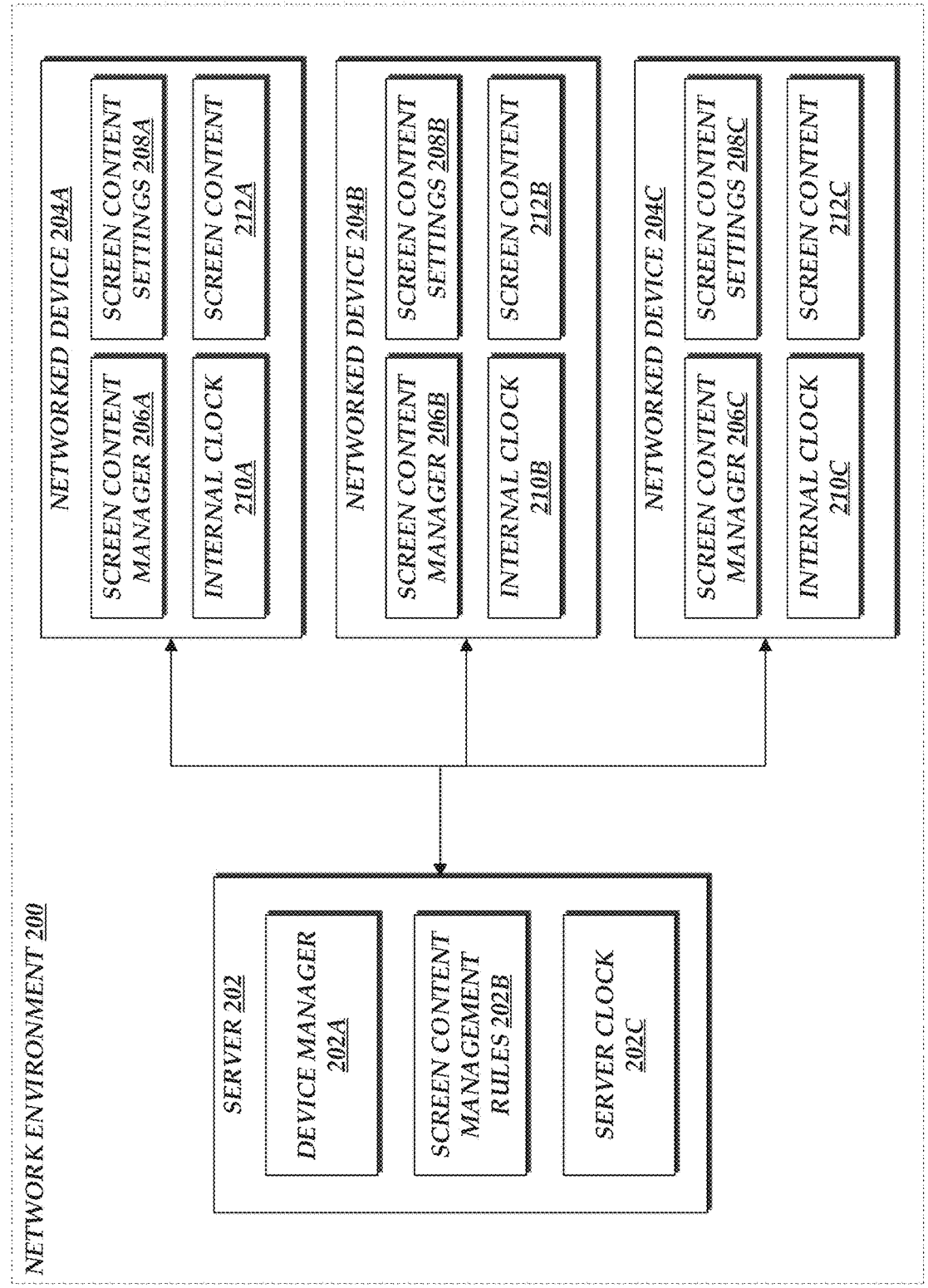
FIG. 2 is a block diagram illustrating components of an example network environment in accordance with aspects of the present disclosure.

FIG. 2 is a block diagram of an example network environment 200, which includes an arrangement of computer hardware and software components that may be used to implement aspects of the present disclosure. The network environment 200 may include many more (or fewer) elements and/or sub-elements than those shown in FIG. 2. It is not necessary, however, that all of these elements be shown in order to provide an enabling disclosure. As illustrated in FIG. 2, the network environment 200 includes a server 202 and networked devices 204A-C (collectively referred to herein as networked device 204 or networked devices 204).

Server

The server 202 includes a device manager 202A configured to manage the networked devices 204, screen content management rules 202B governing how screen content displayed and changed on networked devices 204, and a server clock 202C configured to maintain a reference time for the network environment 200. The server 202 may include additional components not illustrated in FIG. 2. In some embodiments, the server 202 may omit one or more of the components illustrated in FIG. 2.

The device manager 202A may be a software module or application that is configured to perform certain control functions with respect to the networked devices 204. In some embodiments, the device manager 202A is a computing device including circuitry for executing computer instructions and performs one or more functions described herein (e.g., sending clock information to the individual networked devices, sending screen content settings or parameters to the individual networked devices, etc.). The device manager 202A generally initiates, performs, coordinates, and/or controls various management operations with respect to the networked devices 204.

The screen content management rules 202B may include one or more parameters to be used to control the screen content display at the individual networked devices. For example, the screen content management rules 202B may specify which information, metrics, or other screen content should be displayed and the order in which such information should be displayed on the individual networked devices. In a clinical care setting, the screen content management rules 202B may specify that the networked devices in Clinical Care Area X (e.g., emergency room) should display metrics A, B, and D for 5 seconds each (e.g., display A for 5 seconds, then display B for 5 seconds, then display D for 5 seconds, and then display A again for 5 seconds, etc.), and that networked devices in Clinical Care Area Y (e.g., intensive care unit) should display metrics A and E, 10 seconds each (e.g., display A for 10 seconds, then display E for 10 seconds, then display A again for 10 seconds, etc.).

The server clock 202C may be a clock that keeps track of a reference time to which the individual networked devices in the network environment are synchronized. For example, the reference time according to the server clock 202C may be transmitted to the networked devices 204 according to a schedule (e.g., periodically), based on a user input received by the server 202, or in response to a request received from the individual networked devices 204. For example, a screen content manager of the networked device 204 may be configured to request the reference time from the server 202 according to a schedule (e.g., every 24 hours, every week, every month, etc.) or based on a user input received by the networked device 204.

Although the server 202 is illustrated in FIG. 2 as including the server clock 202C that keeps track of the reference time for the networked devices 204, in other embodiments, the network environment 200 may not include the server 202, and the networked device 204 may synchronize or calibrate its internal clock by communicating an entity outside the network environment 200. In some cases, the networked device 204 does not synchronize or calibrate its internal clock by communicating with another entity.

Networked Device

The networked device 204A includes a screen content manager 206A, screen content settings 208A, an internal clock 210A, and screen content 212A. The networked device 204B includes a screen content manager 206B, screen content settings 208B, an internal clock 210B, and screen content 212B. The networked device 204C includes a screen content manager 206C, screen content settings 208C, an internal clock 210C, and screen content 212C. In the present disclosure, networked devices 204A-C may individually or collectively be referred to as networked device 204 or networked devices 204, screen content managers 206A-206C may individually or collectively be referred to as screen content manager 206 or screen content managers 206, screen content settings 208A-208C may individually or collectively be referred to as screen content settings 208, internal clock 210A-210C may individually or collectively be referred to as internal clock 210 or internal clocks 210, and screen contents 212A-212C may individually or collectively be referred to as screen content 212 or screen contents 212. The networked device 204 may include additional components not illustrated in FIG. 2. For example, the networked device 204 may include one or more components configured to perform a medical function such as delivering a drug to a patient or monitoring such delivery. In some embodiments, the networked device 204 may omit one or more of the components illustrated in FIG. 2.

The screen content manager 206 may be a software module or application that is configured to perform certain functions described herein as being performed by the networked devices 204. In some embodiments, the screen content manager 206 includes circuitry for executing computer instructions and performs one or more functions described herein.

The screen content settings 208 may include one or more parameters to be used to control the screen content display at the individual networked devices. Such parameters may be received from the server 202 or inputted at the networked device 204.

The internal clock 210 may be a clock maintained by the networked device 204, and the internal clock 210 in the individual networked devices may periodically be synchronized with the server clock 202C at the server 202. Such synchronization may occur according to a schedule (e.g., periodically), based on a user input received by the server 202, or based on a user input received by the networked device 204. For example, the screen content manager 206 may be configured to request the reference time from the server 202 according to a schedule (e.g., every 24 hours, every week, every month, etc.) or based on a user input received by the networked device 204.

In some embodiments, the internal clock 210 of the individual networked devices are synchronized with the server clock 202C dynamically based on how quickly the internal clock 210 becomes out of sync. For example, when the networked device 204A sends a clock synchronization request to the server 202, and the server 202 transmits a clock synchronization signal to the networked device 204A, the networked device 204A may update the internal clock 210A using the received clock synchronization signal. In some cases, instead of updating the internal clock 210A, the networked device 204 may calculate an offset between the server clock 202C and the internal clock 210A, and apply the offset when determining the current time (e.g., for identifying the screen content to be displayed). Additionally, the networked device 204A may calculate the difference between the time according to the internal clock 210A prior to the synchronization and the time indicated by the clock synchronization signal (or the time according to the server clock 202C). If the difference is greater than a threshold amount (e.g., 1 second, 5 seconds, 10 seconds, etc.), the networked device 204A may increase the frequency at which the networked device 204A requests synchronization of the internal clock 210A with the server clock 202C. For example, if the time elapsed between the last two synchronizations was 5 days, and the time difference was 2 seconds, the networked device 204A may request the next synchronization 2 or 3 days (e.g., less than 5 days) after the most recent synchronization. If the networked device 204A determines that, after synchronizing the clocks 2 days after the most recent synchronization, the time difference fell below the threshold amount of drift (e.g., 1 second), then the networked device 204A may continue to request synchronization every 2 days. If the time difference was still above the threshold amount of drift, the networked device 204A may further increase the synchronization frequency (e.g., to 1 day, to 12 hours, or some other duration less than 2 days).

In some embodiments, the individual networked devices each have a different synchronization schedule. For example, the networked device 204A may request synchronization every 2 days, the networked device 204B may request synchronization every 3 days, and the networked device 204C may request synchronization every 5 days. In such cases, the time at which the individual networked devices are synchronized with the server clock 202C may not be identical or may not overlap with each other. In some embodiments, the schedule at which the individual networked devices are synchronized with the server clock 202C is non-periodic. In some cases, the threshold amount of drift is set to a value that is substantially lower than the content display period (e.g., 1%, 5%, 10%, etc.). For example, if the metrics are rotated every 10 seconds, the difference of 0.1 second among the display times of the networked devices may be acceptable or negligible (e.g., the networked device 204A switching from "volume infused" to "rate" at 11:20:00.01 in reference time and the networked device 204B switching from "volume infused" to "rate" at 11:20:00.00 in reference time, where the networked devices continue to display "rate" until 11:20:10.01 and 11:20:10.00 in reference time, respectively). Although some examples of clock synchronization were described as being requested by the networked devices, in other examples, the clock synchronization may be requested by the server 202.

Time according to the internal clocks of the individual networked devices may be measured from the same reference point. For example, each internal clock is configured to output a current time indicative of the number of seconds elapsed since year 1900 (e.g., over 3 million seconds). In some embodiments, the reference point shared by the internal clocks is periodically updated so that time-based calculations involve smaller numbers. Although some clock synchronization techniques described with reference to FIG. 2 uses a server clock 202C, in some implementations, the internal clocks 210 may be synchronized using a network time protocol (NTP). In such implementations, the networked devices 240 may communicate with an NTP server to update their internal clocks 210 (e.g., periodically or aperiodically). Alternatively or additionally, the networked devices 240 may synchronize the internal clocks 210 using an atomic clock.

The screen content 212 may include one or more metrics calculated or maintained by the individual networked devices. For example, such metrics may include the volume of the medication infused so far, the volume of the medication to be infused, the rate at which the medication is being infused, and the like. The metrics may also include any other metrics or parameters described herein.

Centralized Display

In some embodiments, the network environment 200 of FIG. 2 may include a centralized display that can display the screen content associated with multiple networked devices 204. For example, the screen of the centralized display may be divided into multiple portions that can each display the screen content associated with a specific networked device 204. In some cases, the multiple networked device 204 whose screen content is displayed on the centralized display may be from multiple geographic locations (e.g., two or three different CCAs) and as a result may be configured to cycle through different metrics in different display order. In some embodiments, the centralized display may display the same metric for each networked device 204 whose screen content is displayed on the centralized display. For example, if the networked devices 204 in an emergency room are configured to cycle through rate and time, and the networked device 204 in an intensive care unit are configured to cycle through rate and dose, the centralized display configured to display the screen content associated with all of the networked devices 204 in the emergency room and the intensive care unit may cycle through rate, time, and dose for all such networked devices 204 (e.g., a union of the different sets of metrics). In some cases, the centralized display may cycle through all of the available metrics regardless of the characteristics of the individual networked devices 204. Alternatively, the centralized display may not display the same metric for each networked device 204, and cycle through rate and time for the networked devices 204 in the emergency room and cycle through rate and dose for the networked devices 204 in the intensive care unit. In some implementations, the centralize display provides an indication of the CCA associated with the individual metrics displayed on the centralized display. For example, the metrics associated with the networked devices 204 in the emergency room may look different from the metrics associated with the networked devices 204 in the intensive care unit (e.g., in location, in size, in color, based on presence of indicators, etc.). The centralized display may be connected to the server 202, or to another server not illustrated in FIG. 2 that is in network communication with the server 202.

Architecture of Networked Device

Figure 3:
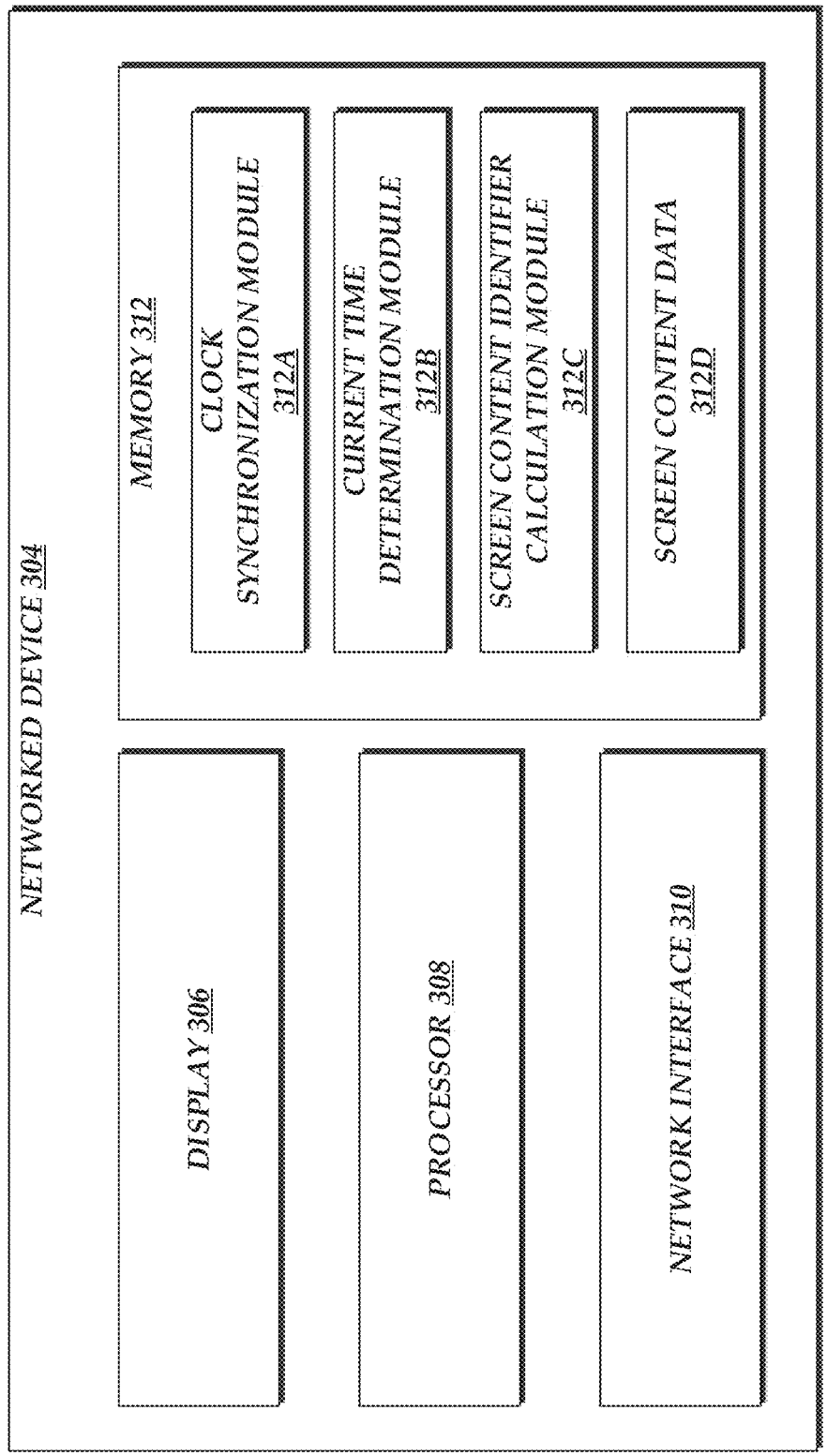
FIG. 3 illustrates a general architecture of an example networked device in accordance with aspects of this disclosure.

With reference to FIG. 3, the components of an example networked device are described in greater detail. The example architecture of the networked device 304 depicted in FIG. 3 includes an arrangement of computer hardware and software modules that may be used to implement aspects of the present disclosure. The networked device 304 may include many more (or fewer) elements and/or sub-elements than those shown in FIG. 3. It is not necessary, however, that all of these elements be shown in order to provide an enabling disclosure.

As illustrated, the networked device 304 includes a display 306, a processor 308, a network interface 310, and a memory 312, all of which may communicate with one another by way of a communication bus. The display 306 may display information generated or stored by the networked device 304 or any other information associated with the networked device 304. For example, the networked device may be an infusion pump being used to deliver medication to a patient. In such a case, the display 306 may display the volume of the medication infused so far, the volume of the medication to be infused, the rate at which the medication is being infused, and the like. The processor 308 may receive information and instructions from other computing systems or services via a network. The processor 308 may also transmit information to and receive information from the memory 312 and further provide content to the display 306 for display. The network interface 310 may provide connectivity to one or more networks or computing systems in the network environment described herein. For example, the network interface 310 may be a serial port, a parallel port, or any other communication interface that can enable or facilitate wired or wireless communication according to any communication protocols such as Zigbee (e.g., IEEE 802.15.4), Bluetooth, Wi-Fi (e.g., IEEE 802.11), Near Field Communication (NFC), and the like.

The memory 312 may contain computer program instructions (grouped as modules in some embodiments) that the processor 308 can execute in order to implement one or more aspects of the present disclosure. The memory 312 may include RAM, ROM, and/or other persistent, auxiliary, or non-transitory computer-readable media. In some embodiments, the memory 312 stores an operating system that provides computer program instructions for use by the processor 308 in the general administration and operation of the networked device 304. As illustrated in FIG. 3, the memory 312 may include a clock synchronization module 312A, a current time determination module 312B, a screen content identifier calculation module 312C, and screen content data 312D. In some embodiments, the clock synchronization module 312A, the current time determination module 312B, and the screen content identifier calculation module 312C may, when executed by the processor 308, individually or collectively implement various aspects of the present disclosure. Although shown as distinct modules, in some embodiments, the division of the modules into the clock synchronization module 312A, the current time determination module 312B, and the screen content identifier calculation module 312C is logical in nature, and a single software application executing on the networked device 304 may, when executed by the processor 308, perform some or all of the steps described as being performed by the modules. For example, each of the clock synchronization module 312A, the current time determination module 312B, and the screen content identifier calculation module 312C may be part of the screen content manager 206.

The clock synchronization module 312A facilitates synchronization between the server clock 202C and the internal clocks maintained by the individual networked devices 204. The current time determination module 312B facilitates determination of the current time associated with the internal clock 210. For example, the current time determination module 312B may determine the current time indicated by the internal clock 210 maintained and updated by the clock synchronization module 312A. The screen content identifier calculation module 312C facilitates determination of the screen content to be displayed at any given time. For example, the screen content identifier calculation module 312C calculates a screen content identifier based on the current time determined by the current time determination module 312B.

Although not shown in FIG. 3, the networked device 304 may further include one or more input devices such as a touch screen, mechanical buttons, or a voice recognition system. Further, the networked device 304 may include one or more additional storage devices for storing data generated by the networked device 304 or other data utilized in implementing aspects of the present disclosure.

Near View and Far View

Graphical user interfaces for medical devices that display patient and treatment information have improved clinician efficiency when caring for patients. However, a challenge for designing graphical user interfaces is balancing the amount of information displayed with readability and user-friendliness. Presenting too much information may impede the interaction between the user and the device. In some embodiments, two screen modes may be utilized to present more information when the user is interacting with the device in one mode (e.g., "near view"), and to present less information when the user is simply viewing the device from far away (e.g., "far view"). Near view screens may present user interface buttons, fields, and keys to allow the user to input various commands, whereas far view screens may simply show a single metric that the user may be interested in reviewing from far away. Far view screens may be activated after a period of inactivity (e.g., lack of user input) and may cycle through numerous metrics that are relevant to the clinical setting.

Comparison of Synchronized and Non-Synchronized Displays

Figure 4:
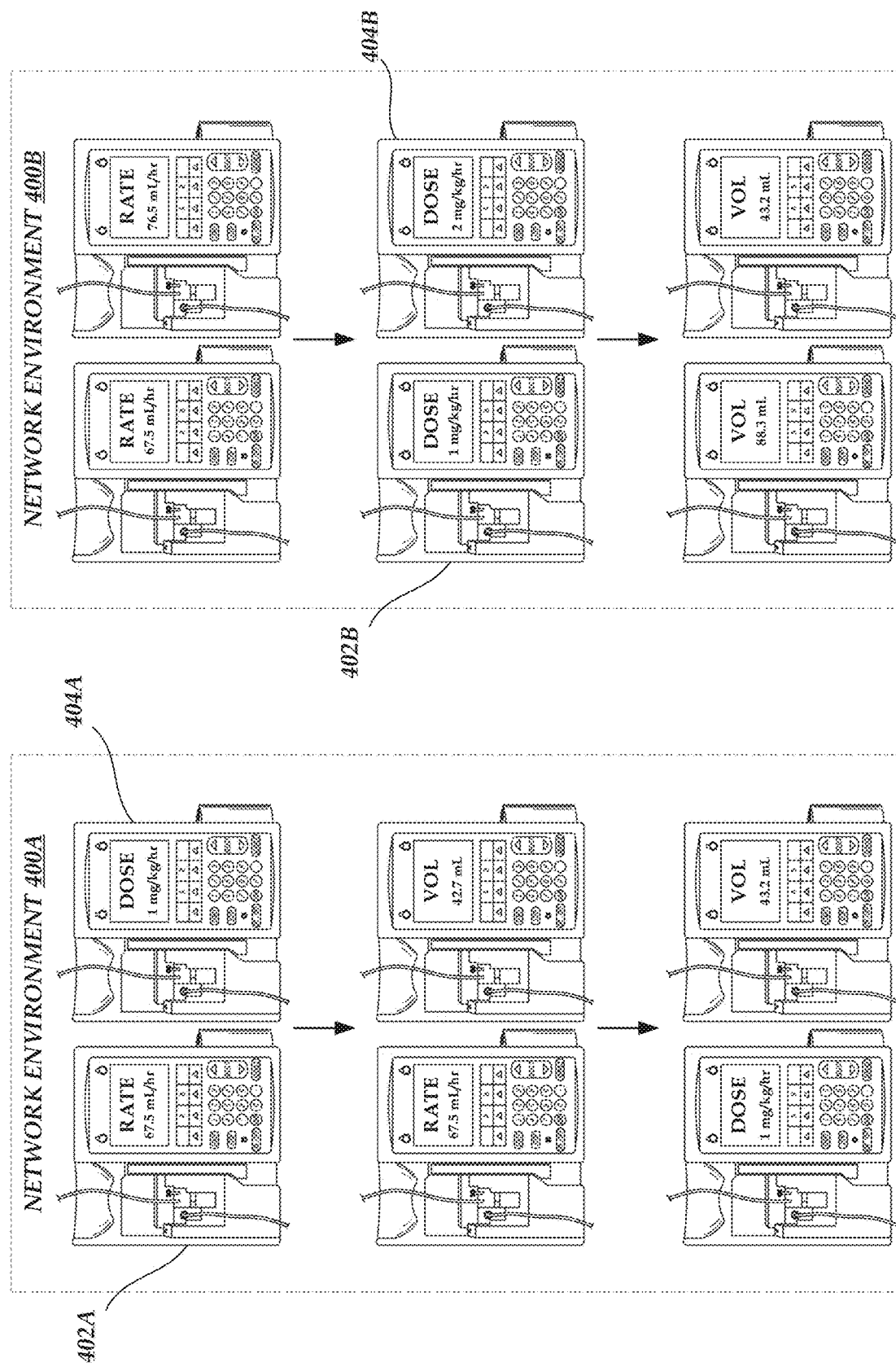
FIG. 4 illustrates example networked devices in network environments in accordance with aspects of this disclosure.

With reference now to FIG. 4, example network environments 400A and 400B will be described. The network environment 400A includes networked devices 402A and 404A that are positioned side by side, and the network environment 400B includes networked devices 402B and 404B that are positioned side by side.

In the top row in FIG. 4, the display of the networked device 402A shows the rate at which the medication is being delivered to the patient, and the display of the networked device 404A shows the time remaining until the medication delivery is finished. As shown, the displays of the networked devices 402A and 40A are not in sync with each other, since the screen content (e.g., the type of metric displayed) of the networked device 402A does not match the screen content (e.g., the type of metric displayed) of the networked device 404A. When the displays of the networked devices are not in sync, it is difficult for the caregiver (e.g., doctor or nurse) to quickly scan the displays and gather relevant information from multiple networked devices, especially if a large number of networked devices are present in the room.

In FIG. 4, the arrows between the rows in FIG. 4 indicate the passage of time (e.g., 1 second, 5 seconds, 1 minute, etc.). After some time has passed, in the middle row, the display of the networked device 402A continues to show the rate, whereas the display of the networked device 404A switches to displaying the volume infused. As illustrated, not only are the two displays out of sync, they also switch at different times.

After some additional time has passed, in the bottom row, the display of the networked device 402A switches to displaying the time remaining, whereas the display of the networked device 404A continues to show the volume infused. When the displays of the networked devices switch to different screen content at different times, it is difficult for the caregiver (e.g., doctor or nurse) to quickly scan the displays and gather relevant information from multiple networked devices, especially if a large number of networked devices are present in the room.

In contrast, as illustrated in FIG. 4, the displays of the networked devices 402B and 404B of the network environment 400B are in sync with each other (e.g., both displaying the rate in the top row, the time remaining in the middle row, and the volume infused in the bottom row). Further, the displays of the networked devices 402B and 404B switch to the next metric at the same time (or at substantially the same time). Thus, the displays of the networked devices 402B and 404B are much easier for a caregiver to scan, especially from afar in a room filled with a large number of such networked devices.

Screen Content Update Method

Figure 5:
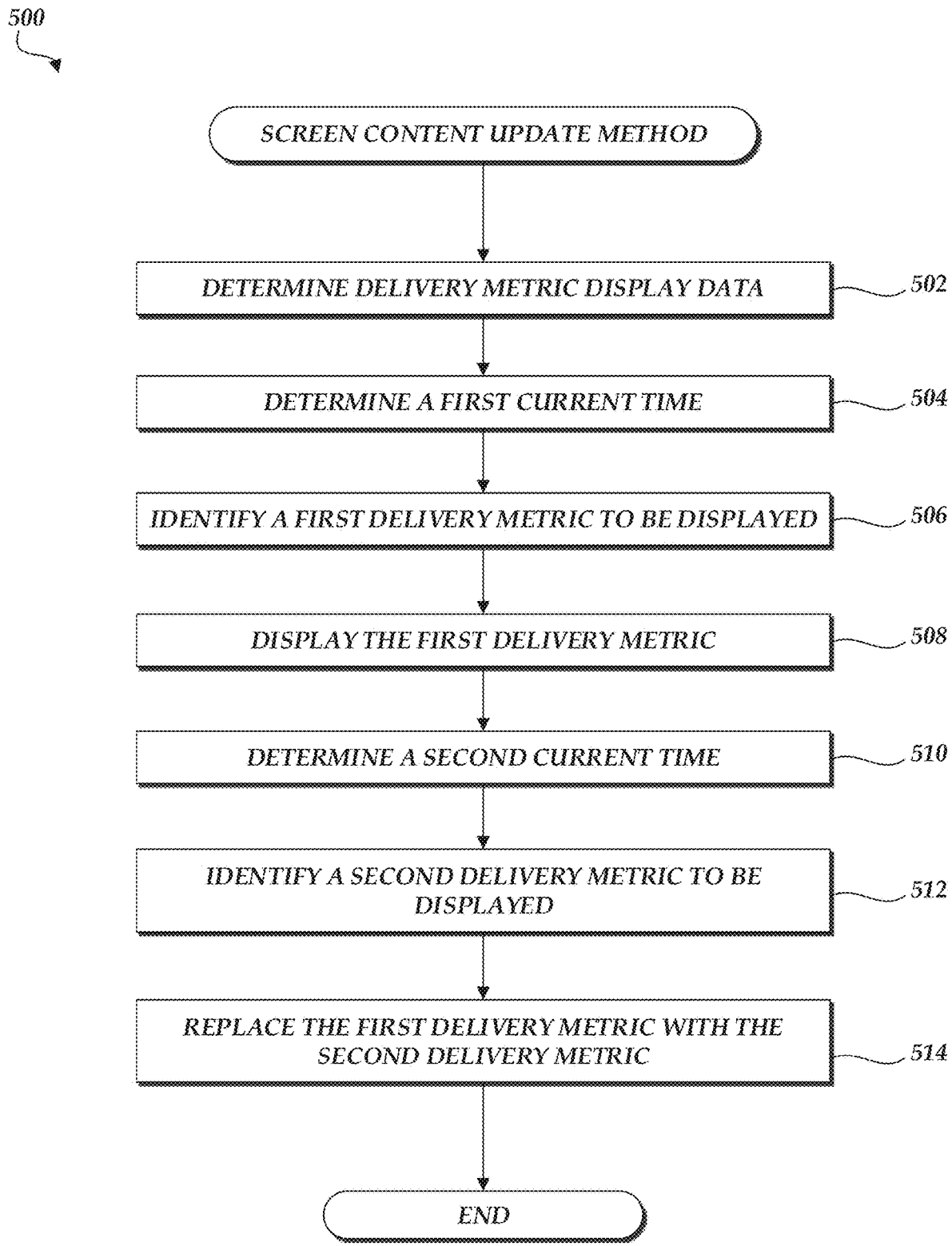
FIG. 5 illustrates an example screen content update method in accordance with aspects of this disclosure.

With reference now to FIG. 5, an example screen content update method 500 will be described. The example method 500 may be carried out, for example, by the networked device 204 of FIG. 2 (or one or more components thereof) or the networked device 304 of FIG. 3 (or one or more components thereof). The method 500 illustrates an example algorithm that may be programmed, using any suitable programming environment or language, to create machine code capable of execution by a CPU or microcontroller of the networked device 204. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the networked device 204 that is coupled to the CPU or microcontroller and then then executed by the CPU or microcontroller. For convenience, the steps of the example method 500 are described as being performed by the networked device 204.

At block 502, the networked device 204 determines delivery metric display data from the server 202. The delivery metric display data may include information needed or used to identify the screen content to be displayed on the networked device 204. For example, the delivery metric display data may include the identity and type of delivery metrics to be displayed and the duration for which each delivery metric is to be displayed. In some embodiments, the server 202 has a record of the CCA in which the networked device 204 is located, and the server 202 transmits, based on the CCA associated with the networked device 204, data indicative of which one(s) of the available metrics should be displayed on the networked device 204. For example, the networked device 204 may transmit data indicative of the CCA of the networked device 204 to the server 202 upon entry (e.g., by a caregiver) or detection (e.g., using one or more sensors on the networked device 204) of the CCA. Alternatively, some or all of the delivery metric display data may not be received, and a corresponding default value may be used. For example, if the delivery metric display data received from the server 202 includes an indication of the identity of the delivery metrics to be displayed, but does not include the duration for which each delivery metric is to be displayed, a default value stored on the networked device 204 may be used (e.g., 5 seconds, 10 seconds, or any other value). In some cases, the delivery metric display data may be provided to the networked device 204 by other means such as manual input from a user, copied from a storage device, and so on. The networked device 204 may receive the delivery metric display data from the server 202 according to a predetermined schedule, periodically or aperiodically. In some embodiments, the networked device 204 may receive the delivery metric display data from another source, such as an internal or external storage device or via a manual input from the user of the networked device 204.

At block 504, the networked device 204 determines a first current time based on the internal clock 210. For example, the networked device 204 may determine the current time in response a determination that the screen content should be changed. Such a determination may be made by the networked device 204 in response to detecting a period of inactivity (e.g., when the networked device 204 is switching to screen saver mode). Alternatively or additionally, such a determination may be made by the networked device 204 according to a schedule (e.g., every 5 seconds, every 10 seconds, every minute, etc.). The current time determined using the internal clock 210 may be in the traditional hh:mm:ss format. In other cases, the current time is represented in hours, minutes, seconds, milliseconds, or another unit of time.

At block 506, the networked device 204 identifies a first delivery metric to be displayed on the display of the networked device 204. Identifying the first delivery metric may involve calculating a delivery metric index value and determining the first delivery metric using the delivery metric index value (e.g., by indexing into a list of delivery metrics). For example, if the calculated delivery metric index value is 3, and the list of delivery metrics maintained by the networked device 204 is {dose, rate, volume infused, volume to be infused, time remaining}, the networked device 204 may identify "volume to be infused" as the first delivery metric. Although relevant metrics for an infusion pump are used in this example, any other number and type of metrics, statistics, or information may be cycled through via the display of the networked device 204.

In some embodiments, the delivery metric index value is calculated as follows:

$$\text{(delivery metric index value)} = \text{trunc}\left(\frac{(T_{elapsed\_seconds\_in\_system\_time} \bmod (N_{metrics\_available} * T_{display\_period\_length}))}{T_{display\_period\_length}}\right) \quad \text{Equation(1)}$$

$$\text{(delivery metric index value)} = \text{trunc}\left(\frac{(T_{elapsed\_seconds\_in\_system\_time} \bmod (N_{metrics\_available} * T_{display\_period\_length}))}{T_{display\_period\_length}}\right) + 1 \quad \text{Equation (2)}$$

In Equation (1), $T_{elapsed\_seconds\_in\_system\_time}$ represents the number of seconds elapsed according to the internal clock maintained by the networked device 204, $N_{metrics\_available}$ represents the number of metrics available for display, and $T_{display\_period\_length}$ represents the length of each content display period in seconds.

"trunc" represents the truncation operation, which removes the digits right of the decimal point. For example, trunc (3.5) would equal 3. "mod" represents the modulo operation, which finds the remainder after division of one number by another. For example, 7 mod 3 would equal 1, since 7 divided by 3 would leave a quotient of 2 and a remainder of 1.

Equation (2) is a variation of Equation (1), and the only difference is that 1 is added such that the lowest value of (delivery metric index value) is 1 instead of 0. In Equation (1), "delivery metric index value" of 0 corresponds to the first one of the available metrics, and in Equation (2), "delivery metric index value" of 1 corresponds to the first one of the available metrics.

Although $T_{elapsed\_seconds\_in\_system\_time}$ is used in Equation (1), in some embodiments, the current time used to identify the first delivery metric is not in seconds but in a different unit (e.g., milliseconds, minutes, hours, or some other temporal unit). In some cases, $N_{metrics\_available}$ represents the number of all metrics that the networked device 204 is configured to display. For example, if the networked device 204 is configured to cycle through {dose, rate, volume infused, volume to be infused, time remaining} every time, the networked device 204 may determine that $N_{metrics\_available}$ is equal to 5. In other cases, $N_{metrics\_available}$ represents the number of metrics in a subset that includes some but not all of the metrics that the networked device 204 is configured to display. The metrics in such a subset may be determined based on one or more conditions (e.g., location of the networked device 204, CCA, class or type of medication, or any other parameter associated with the networked device 204). For example, based on a determination that the CCA associated with the networked device 204 is "neonatal intensive care unit" and based on a determination that only {dose, volume infused, volume to be infused} should be displayed for "neonatal intensive care unit," the networked device 204 may determine that the number of metrics in the subset is 3 (e.g., out of 5 metrics). In some embodiments, the networked device 204 downloads the number and type of metrics to be displayed for a given CCA and the length of the content display period for the given CCA from the server 202. Such a download may take place upon the CCA of the networked device 204 being entered or changed by a user of the networked device 204 (e.g., caregiver, administrator, operator, etc.).

Table 1 illustrates example calculations for identifying screen content to be displayed. For this particular networked device 204, three metrics are to be displayed in sequence for 2 seconds each. As shown in Table 1, for the 2000$^{th}$ and 2000 seconds (e.g., from 2000.00 seconds in system time through 2001.99 in system time), the metric corresponding to an index value of "1" is displayed, for the 2002$^{nd}$ and 2003$^{rd}$ seconds, the metric corresponding to an index value of "2" is displayed, and for the 2004$^{th}$ and 2005$^{th}$ seconds, the metric corresponding to an index value of "0" is displayed, and for the 2006$^{th}$ and 2007$^{th}$ seconds, the metric corresponding to an index value of "1" is displayed again, for the 2008$^{th}$ second, the metric corresponding to an index value of "2" is displayed again, and so on. According, in the example of Table 1, three variables (labeled A, B, and C) are used to identify the screen content to be displayed at a given point in time.

TABLE 1

Example calculations for identifying screen content to be displayed

| | | | | | | | | | |
|---|---|---|---|---|---|---|---|---|---|
| A: number of metrics | | | | | 3 | | | | |
| B: content display period (in seconds) | | | | | 2 | | | | |
| C: current time (in seconds) | 2000 | 2001 | 2002 | 2003 | 2004 | 2005 | 2006 | 2007 | 2008 |
| C mod (A*B) | 2 | 3 | 4 | 5 | 0 | 1 | 2 | 3 | 4 |
| (C mod (A*B))/B | 1 | 1.5 | 2 | 2.5 | 0 | 0.5 | 1 | 1.5 | 2 |
| trunc ((C mod (A*B))/B) | 1 | 1 | 2 | 2 | 0 | 0 | 1 | 1 | 2 |

At block 508, the networked device 204 displays the first delivery metric identified at block 506. The display of the first delivery metric may occur at a first time and may continue for the duration (e.g., content display period) specified by the delivery metric display data (or a default duration). Based on the duration for which the first delivery metric is to be displayed, the networked device 204 may perform the following steps such that the display of the delivery metric to be displayed immediately subsequent to the first delivery metric (e.g., the second delivery metric identified at block 512) occurs at a second time that is a specific time period equal to the duration away from the first time at which the first delivery metric was displayed. In some embodiments, none of blocks 504-508 is performed in response to a request, instruction, signal, or communication from the server 202. Alternatively, in some other embodiments, one or more of blocks 504-508 are performed in response to a request, instruction, signal, or communication from the server 202.

At block 510, the networked device 204 determines a second current time based on the internal clock 210. For example, the networked device 204 may determine the current time in response a determination that the screen content should be changed. The determination that the screen content should be changed may be made periodically (e.g., at every second, before each second expires, etc.). In some cases, the networked device 204 may start a timer (e.g., an event timer based on a hardware interrupt or a software interrupt) at the first time at which the first delivery metric is displayed for the duration for which the first delivery metric is to be displayed. When the timer expires, the networked device 204 may determine the second current time. In some cases, the networked device 204 may determine the second current time a specific time period (e.g., 1 second, 5 seconds, or any other time period) before the timer expires. Alternatively, the networked device 204 may set the timer for a duration that is shorter than the duration for which the first delivery metric is to be displayed by a specific time period (e.g., 1 second, 5 seconds, or any other time period). In some cases, the networked device 204 may set the timer at the time of determining the first delivery metric. In some other cases, the networked device 204 may calculate the second current time by adding the duration for which the first delivery metric is to be displayed to the first current time determined at block 504. In such cases, the networked device 204 may determine the current time based on the internal clock 210 once in connection with the initially displayed screen content, and determine the timing of each subsequent screen content by (without accessing the internal clock 210) adding the content display period (e.g., 5 seconds) to the time at which the initially displayed screen content is to be replaced with the next screen content (which can be, for example, 3 seconds from the time the screen content is initially displayed). The networked device 204 may determine the display order based on the predetermined order in which the different screen contents or metrics are arranged (e.g., in the order that the delivery metrics appear in FIG. 7, or in some other order). By not having to re-calculate the display metric index at every second or at every content display period, processing power and other computing resources used to update the screen content can be reduced. Alternatively, by accessing the internal clock 210 at every second or at every content display period, the screen content update process can be more fault-tolerant (e.g., if the networked device 240 for some reason displays the wrong screen content for one content display period, the networked device 240 can still display the correct screen content at the next content display period because the networked device 240 does not rely on any determinations from the previous content display period.)

At block 512, the networked device 204 identifies a second delivery metric to be displayed on the display of the networked device 204. In some embodiments, the networked device 204 determines the second delivery metric using one or more techniques described above in connection with block 506. In other embodiments, the networked device 204 identifies the second delivery metric by determining the next delivery metric in a list that includes all the delivery metrics to be displayed (e.g., cycled through) by networked device 204. For example, in the example illustrated in Table 1, after determining that the delivery metric to be displayed for the $2000^{th}$ second is delivery metric "1", the networked device 204 may determine that the second delivery metric is the next one in the list of delivery metrics (e.g., delivery metric "2" if the list contains more than 2 items, or delivery metric "0" if the list contains only two items).

At block 514, the networked device 204 replaces the first delivery metric displayed on the display with the second delivery metric identified at block 512. Although not illustrated in FIG. 5, blocks 510-514 may be repeated to identify and display additional delivery metrics on the networked device 204. The method 500 may end upon detecting a user input on the networked device 204, upon detecting an error or interrupt routine, upon finishing a given task (e.g., infusion pump finishing the delivery of medication to the patient) or after a predetermined time period. In some embodiments, none of blocks 510-514 is performed in response to a request, instruction, signal, or communication from the server 202. Alternatively, in some other embodiments, one or more of blocks 510-514 are performed in response to a request, instruction, signal, or communication from the server 202.

In the method 500, one or more of the blocks shown in FIG. 5 may be removed (e.g., not performed) and/or the order in which the method 500 is performed may be switched. In some embodiments, additional blocks may be added to the method 500. For example, although not shown in FIG. 5, the networked device 204 may receive reference time information from the server 202 and synchronize its internal clock based on the received information. Although the method 500 is described in the context of displaying delivery metrics, the techniques described herein can be extended to displaying other screen content. The embodiments of the present disclosure are not limited to or by the example shown in FIG. 5, and other variations may be implemented without departing from the spirit of this disclosure.

Examples of Networked Devices

Although some embodiments of the present disclosure are described with respect to infusion pumps, the techniques described herein may be extended to other medical devices or networked devices. For example, one or more networked devices describe herein may be patient care monitors configured to display blood pressure, heart rate, blood oxygenation, and the like. Additionally or alternatively, one or more networked devices described herein may be a smartphone or tablet executing an application configured to display the screen content according to one or more aspects of the present disclosure (e.g., based on an internal clock of the smartphone or tablet and based on parameters received from the server 202 or another centralized server). Displaying such screen content may be synchronized with one or more other networked devices in the network environment.

Synchronized Metric Switching Method

Figure 6:
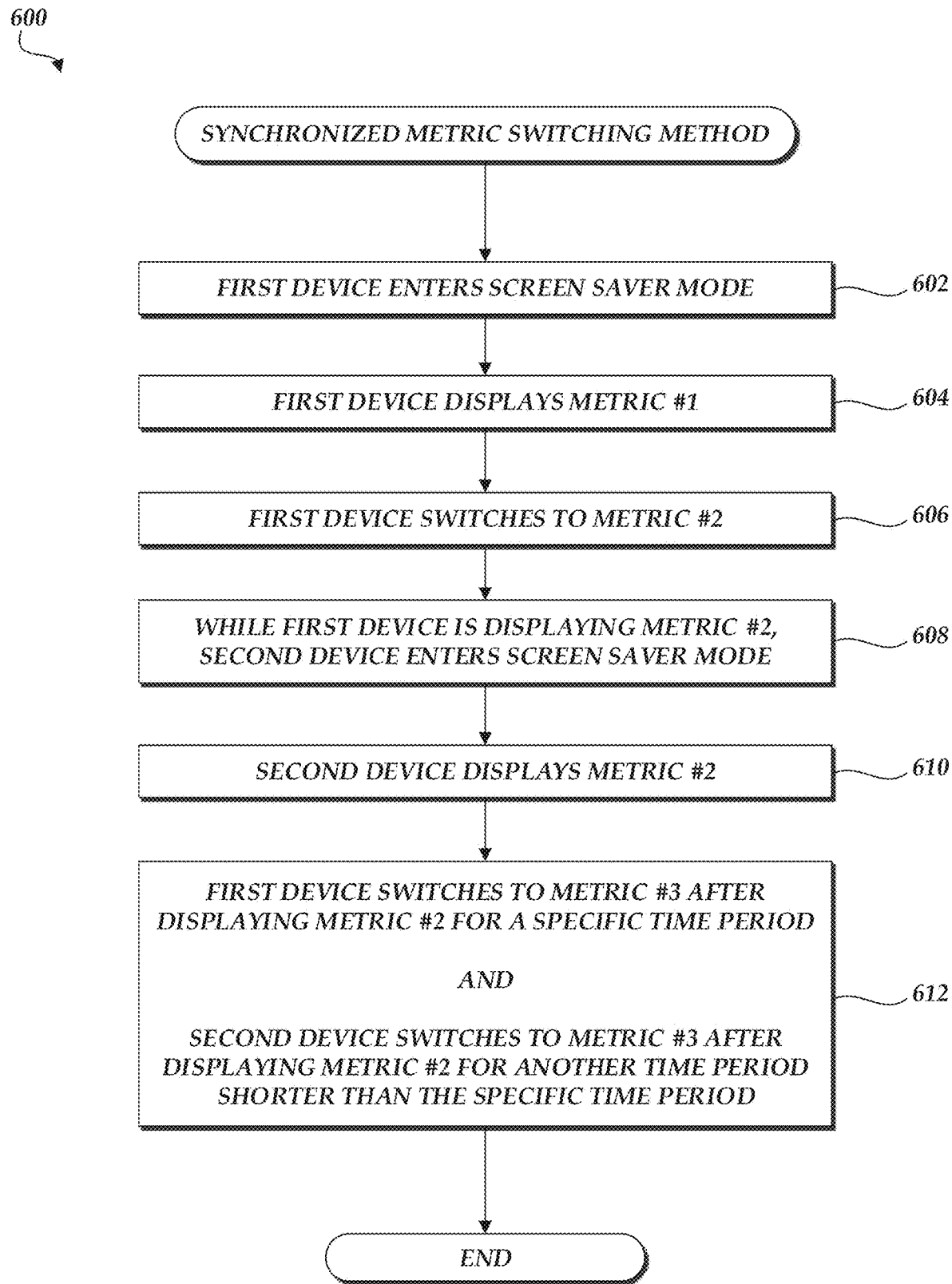
FIG. 6 illustrates an example synchronized metric switching method in accordance with aspects of this disclosure.

With reference now to FIG. 6, an example synchronized metric switching method 600 will be described. The example method 600 may be carried out, for example, by the networked device 204 of FIG. 2 (or one or more components thereof) or the networked device 304 of FIG. 3 (or one or more components thereof). The method 600 illustrates an example algorithm that may be programmed, using any suitable programming environment or language, to create machine code capable of execution by a CPU or microcontroller of the networked device 204. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the networked device 204 that is coupled to the CPU or microcontroller and then then executed by the CPU or microcontroller. For convenience, the steps of the example method 600 are described as being performed by the first networked device and/or the second networked device. In some embodiments, the first and second networked devices share one or more characteristics (e.g., CCA, medication, class of medication, patient, network environment, and/or others).

At block 602, the first networked device enters screen saver mode. The first networked device may enter screen saver mode upon detecting inactivity (or no activity) at the first networked device for a specific time period (e.g., inactivity for 1 minute, for 5 minutes, or for any other duration). Inactivity may include not receiving any user input on the first networked device.

At block 604, the first networked device displays metric #1. For example, the first networked device may identify metric #1 using one or more techniques described above in connection with the method 500. The first networked device may determine, upon entering screen saver mode, the current time associated with its internal clock 210, calculate the metric index value associated with the metric to be displayed, and display the identified metric on its display.

At block 606, the first networked device switches to metric #2. For example, the first networked device may identify metric #2 using one or more techniques described above in connection with the method 500, and replace metric #1 with metric #2.

At block 608, while the first networked device is displaying metric #2, the second networked device enters screen saver mode. The second networked device may enter screen saver mode upon detecting inactivity (or no activity) at the second networked device for a specific time period (e.g., inactivity for 1 minute, for 5 minutes, or for any other duration). Inactivity may include not receiving any user input on the second networked device.

At block 610, the second networked device displays metric #2. For example, the second networked device may identify metric #2 using one or more techniques described above in connection with the method 500. The second networked device may determine, upon entering screen saver mode, the current time associated with its internal clock 210, calculate the metric index value associated with the metric to be displayed, and display the identified metric on its display. Even though the first networked device displayed metric #1 after entering screen saver mode, by the time the second networked device has entered screen saver mode, the internal clocks 210 of the first and second networked devices have reached a time period during which metric #2 should be displayed on both of the first and second networked devices. At the time the second networked device displays metric #2, both of the first and second networked devices are di splaying metric #2.

At block 612, the first networked device switches to metric #3 after displaying metric #2 for a specific time period (e.g., duration for which the first networked device is configured to display metric #2 or each metric). Further, the second networked device switches to metric #3 after displaying metric #2 for another time period that is shorter than the specific time period for which the first networked device displayed metric #2. In some embodiments, the first networked device and the second networked device do not rely on a signal transmitted by the server 202 to determine when to switch to the next metric and the first networked device and the second networked device do not communicate with each other to synchronize the metric switching. In such embodiments, even without such signal from the server 202 or inter-device communication, the first and second networked devices switch to metric #3 at the same time (or at substantially the same time). Alternatively, in some other embodiments, the first networked device and the second networked device do rely on a signal transmitted by the server 202 to determine when to switch to the next metric and/or the first networked device and the second networked device do communicate with each other to synchronize the metric switching.

In some cases, the time at which the first networked device switches to metric #3 is different from the time at which the second networked device switches to metric #3 due to the difference in the internal clock of the first networked device and the internal clock of the second networked device. For example, the time difference may be a non-zero value that is less than 1 second. In some embodiments, a first time difference between the time at which the first networked device switches to metric #3 and the time at which the second networked device switches to metric #3 is equal to a second time difference between the time at which the first networked device subsequently switches from metric #3 to metric #4 and the time at which the second networked device subsequently switches from metric #3 to metric #4. Alternatively, in some other embodiments, a first time difference between the time at which the first networked device switches to metric #3 and the time at which the second networked device switches to metric #3 is different from a second time difference between the time at which the first networked device subsequently switches from metric #3 to metric #4 and the time at which the second networked device subsequently switches from metric #3 to metric #4 (e.g., due to the internal clocks becoming out of sync with the server clock 202C at different rates). Although not illustrated in FIG. 6, blocks 510-514 of FIG. 5 may be performed by each of the first and second networked devices to identify and display additional metrics.

In the method 600, one or more of the blocks shown in FIG. 6 may be removed (e.g., not performed) and/or the order in which the method 600 is performed may be switched. In some embodiments, additional blocks may be added to the method 600. Although the method 600 is described in the context of screen saver mode, the techniques described herein can be extended to screen content switching in any other mode (e.g., when the networked device is turned on, upon detecting user input indicating that the networked device should begin displaying and cycling through screen content, and so on). The embodiments of the present disclosure are not limited to or by the example shown in FIG. 6, and other variations may be implemented without departing from the spirit of this disclosure.

Example User Interface

Figure 7:
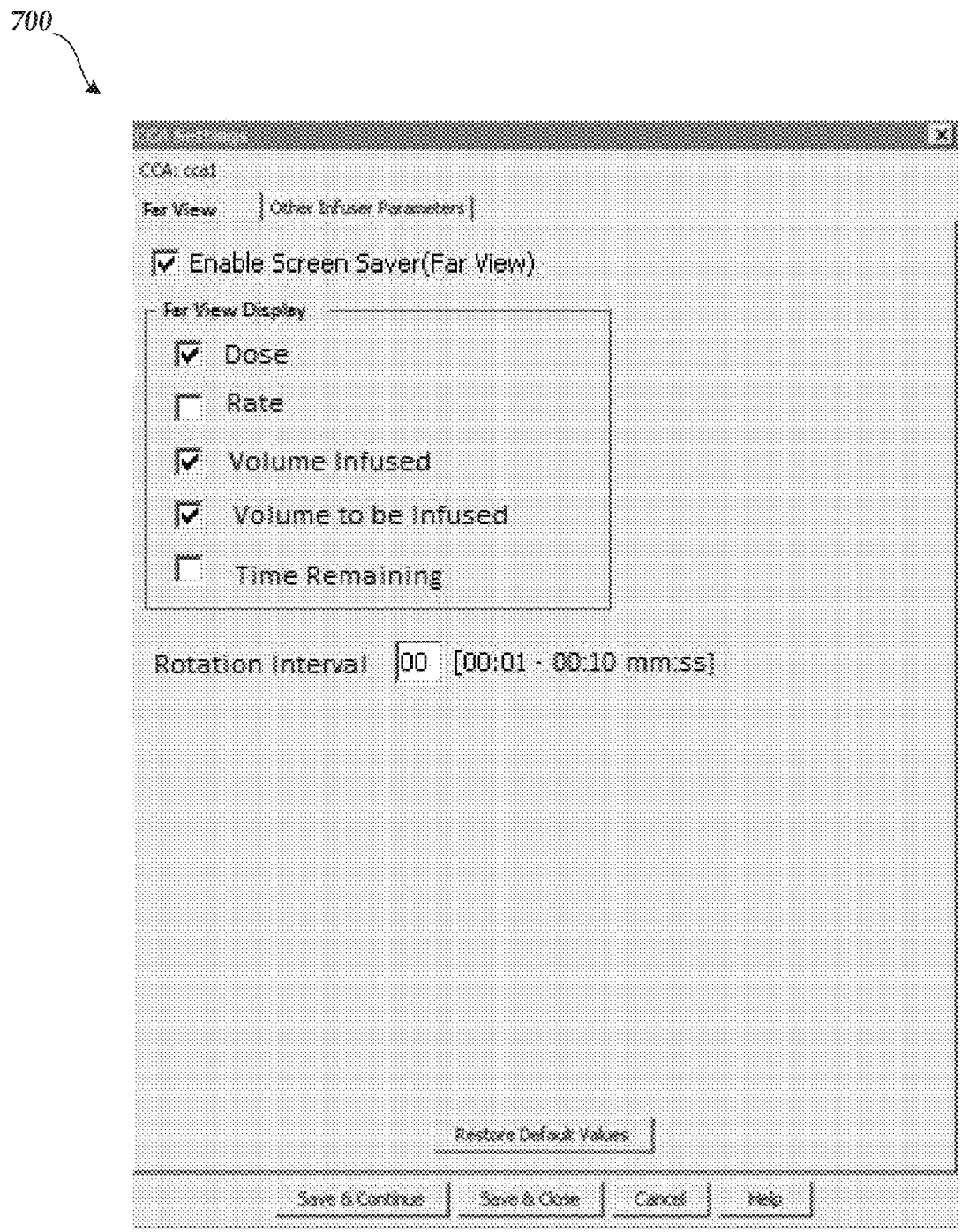
FIG. 7 illustrates an example user interface for specifying the screen content management rules in accordance with aspects of this disclosure.

FIG. 7 illustrates an example user interface 700 for specifying the screen content management rules for a given CCA. As shown, the user interface 700 includes a checkbox for indicating whether screen saver mode is to be enabled for the given CCA, and additional checkboxes for specifying which metrics are to be cycled through in screen saver mode. Further, the user interface 700 includes a field for specifying the content display period (e.g., the duration for which each metric is to be displayed before switching to the next metric). The specified screen content management rules may be transmitted to all of the individual networked devices in the network environment, or only to those associated with the given CCA.

Although the user interface 700 is described in the context of a CCA-specific screen content display scheme, in other embodiments, the screen content display can be specific to one or more other characteristics of the networked device. For example, the number and type of metrics to be cycled through may be drug-specific (e.g., infusion pumps delivering drug "A" may cycle through different type and number of metrics than infusion pumps delivering drug "B"), drug-class-specific (e.g., infusion pumps delivering vasoactive drugs may cycle through different type and number of metrics than infusion pumps delivering anti-infective drugs), CCA-specific (e.g., infusion pumps in operating rooms may cycle through different type and number of metrics than infusion pumps in emergency rooms), patient-specific (e.g., infusion pumps connected to patient "X" may cycle through different type and number of metrics than infusion pumps connected to patient "Y") or any combination-specific such as CCA-drug-specific, CCA-drug-class-specific, and so on (e.g., infusion pumps in operating rooms and delivering vasoactive drugs may cycle through different type and number of metrics than infusion pumps in operating rooms and delivering anti-infective drugs, etc.).

In some embodiments, one or more metrics may not be available for a given drug or drug-class. For example, if the screen content switching is set to be CCA-specific, and networked devices in emergency rooms are configured (e.g., based on the parameters/settings downloaded from the server 202) to cycle through rate, dose, and volume infused. In a particular emergency room, there are two infusion pumps delivering drug "A" and drug "B," respectively. However, if drug "B" cannot be or typically is not administered in a dose-fashion, the infusion pump delivering drug "B" may display the rate for the duration during which the dose is supposed to be displayed. For example, if the screen content switching interval is 10 seconds, the infusion pump delivering drug "A" may display the rate for 10 seconds, the dose for 10 seconds, and the volume infused for 10 seconds and so on. In contrast, the infusion pump delivering drug "B" may display the rate for 20 seconds and the volume infused for 10 seconds and so on (based on the inability to display the dose for drug "B").

Technical Advantages

As described above, in some embodiments, the individual networked devices in the network environment cause their respective screen content to be changed in response to a heartbeat signal received from the server. For example, the server may transmit a heartbeat signal to each networked device every 5 minutes, indicating that the networked device should change the displayed content or display the next content in a given display order. The heartbeat signal may also indicate which content the networked device should display (e.g., by including a content identifier in the heartbeat signal transmitted to the networked device). However, such use of heartbeat signals can consume valuable network resources (e.g., bandwidth) and overwhelm the network, especially if the network includes a large number of such networked devices. Further, processing such heartbeat signals from the server may require a sophisticated processor on the networked device and/or consume valuable processing power. Displaying the screen content based on an internal clock maintained by the individual networked devices and without communicating with the server each time new screen content needs to be displayed, the amount of data transmitted across the network environment may be significantly reduced and valuable network resources and/or processing power can be preserved for other uses.

In other embodiments, the individual networked devices locally store a fixed schedule of which metric to display at what time. In such embodiments, a networked device may store a table that specifies, for each CCA, which metric to display at a given time of day. For example, the table may specify that for networked devices in the ICU should display metric #1 for the first 10 minutes of every hour, metric #2 for the second 10 minutes, metric #3 for the third 10 minutes, and so on, and for networked devices in the OR should display metric #3 for the first 30 minutes of every hour, and metric #4 for the second 30 minutes of every hour. As another example, the table may specify, for each 5-second interval in the 24 hours of a given date, the metric to be displayed for the 5-second interval. However, locally storing such a table would consume a large amount of memory or disk space, which may not be desired for networked devices having limited memory/storage. Also, accessing such a table that is stored remotely over a network can consume valuable network resources (e.g., bandwidth) and overwhelm the network, especially if the network includes a large number of such networked devices. Displaying the screen content based on an internal clock maintained by the individual networked devices and without storing or accessing large amounts of data specifying the screen content to be displayed at any given interval, the amount of storage space needed and/or data transmitted across the network environment may be significantly reduced and valuable storage/network resources can be preserved for other uses.

Example Embodiments

One aspect of the disclosure provides an apparatus configured to deliver medication to patients. The apparatus may include a display, a processor, and a memory. The memory may store an internal clock data according to which one or more delivery metrics are to be displayed on the display. The memory may further store instructions that, when executed by the processor, configure the processor to: receive delivery metric display data from a server in network communication with the apparatus, wherein the delivery metric display data includes a screen change time interval and an indication of one or more delivery metrics to be displayed; in response to a period of inactivity, determine a first current time based on the internal clock data; identify a first delivery metric based on inputting the first current time into a delivery metric determination function, wherein the delivery metric determination function is configured to identify one of a plurality of delivery metrics to be displayed on the display based on the screen change time interval and the indication of the one or more delivery metrics received from the server; cause the first delivery metric to be displayed on the display at a first time; within the screen change time interval from the first time, determine a second current time based on the internal clock data; identify a second delivery metric different from the first delivery metric based on inputting the second current time into the delivery metric determination function; and cause the first delivery metric displayed on the display to be replaced with the second delivery metric at a second time that is not later than the first time by a time period equal to the screen change time.

The apparatus can further include any sub-combination of one or more of the following features: where the instructions, when executed by the processor, further configure the processor to transmit a clock synchronization request to the server, receive a clock synchronization signal from the server, and update the internal clock data based on the clock synchronization signal; where the instructions, when executed by the processor, further configure the processor to transmit the clock synchronization request to the server according to a predefined schedule; where wherein the instructions, when executed by the processor, further configure the processor to determine that a user input has not been received for a threshold amount of time, and in response to the determination that the user input has not been received for the threshold amount of time, determine the first current time based on the internal clock data; where the instructions, when executed by the processor, further configure the processor to calculate a first delivery metric index value based on the first current time and the screen change time interval, and identify the first delivery metric based on the first delivery metric index and the indication of the one or more delivery metrics to be displayed; where the instructions, when executed by the processor, further configure the processor to calculate the first delivery metric index value based on a modulo operation including the screen change time interval and a number of metrics included in the indication of the one or more delivery metrics to be displayed; where the instructions, when executed by the processor, further configure the processor to determine the second current time before an amount of time equal to the screen change time interval has elapsed since the first time; where the instructions, when executed by the processor, further configure the processor to determine the second current time at a time that precedes the second time by a predefined amount of time; where the instructions, when executed by the processor, further configure the processor to within the screen change time interval from the second time, determine a third current time based on the internal clock data, identify a third delivery metric different from the second delivery metric based on inputting the third current time into the delivery metric determination function, and cause the second delivery metric displayed on the display to be replaced with the third delivery metric at a third time that is not later than the second time by the time period equal to the screen change time interval, such that a first time difference between the first time and the second time is shorter than a second time difference between the second time and the third time; and where the second time difference is equal to the screen change time interval, and the first time difference is shorter than the screen change time interval.

One aspect of the disclosure provides a method of providing synchronized screen content. The method may include: receiving, by a networked device in network communication with a server, metric display data from the server, the metric display data including a screen change time interval and an indication of one or more metrics to be displayed; in response to detecting a period of inactivity, determining a first current time associated with an internal clock of the networked device; calculating a first metric index value based on the first current time and the screen change time interval; displaying a first metric associated with the first metric index value on a display of the networked device at a first time; within the screen change time interval from the first time, determining a second current time associated with the internal clock of the networked device; calculating a second metric index value different from the first metric index value based on the second current time; and replacing the first metric displayed on the display of the networked device with a second metric associated with the second metric index value at a second time that is not later than the first time by a time period equal to the screen change time interval.

The method can further include any sub-combination of one or more of the following features: where the method further includes transmitting a clock synchronization request to the server, receiving a clock synchronization signal from the server, and updating the internal clock based on the clock synchronization signal; where the method further includes transmitting the clock synchronization request to the server according to a predefined schedule; where the method further includes determining that a user input has not been received for a threshold amount of time, and in response to determining that the user input has not been received for the threshold amount of time, determining the first current time associated with the internal clock; where the method further includes calculating the first metric index value based on a modulo operation including the screen change time interval and a number of metrics included in the indication of the one or more metrics to be displayed; where the method further includes determining the second current time before an amount of time equal to the screen change time interval has elapsed since the first time; where the method further includes determining the second current time at a time that precedes the second time by a predefined amount of time; where the method further includes, within the screen change time interval from the second time, determining a third current time associated with the internal clock, calculating a third metric index value different from the second metric index value based on the third current time, and replacing the second delivery metric displayed on the display with a third metric associated with the third metric index value at a third time that is not later than the second time by the time period equal to the screen change time interval, such that a first time difference between the first time and the second time is shorter than a second time difference between the second time and the third time; and where the second time difference is equal to the screen change time interval, and the first time difference is shorter than the screen change time interval.

One aspect of the disclosure provides a system adapted to provide synchronized screen content. The system may include a server and a plurality of networked devices in network communication with the server. Each networked device of the plurality of networked devices may be configured to: receive metric display data from the server, the metric display data including a screen change time interval and an indication of one or more metrics to be displayed; in response to a period of inactivity, determine a first current time associated with an internal clock of the networked device; calculate a first metric index value based on the first current time and the screen change time interval; display a first metric associated with the first metric index value on a display of the networked device at a first time; within the screen change time interval from the first time, determine a second current time associated with the internal clock of the networked device; calculate a second metric index value different from the first metric index value based on the second current time; and replace the first metric displayed on the display of the networked device with a second metric associated with the second metric index value at a second time that is not later than the first time by a time period equal to the screen change time interval.

The system can further include any sub-combination of one or more of the following features: where the networked device is further configured to transmit a clock synchronization request to the server, receive a clock synchronization signal from the server, and update the internal clock based on the clock synchronization signal; where the networked device is further configured to transmit the clock synchronization request to the server according to a predefined schedule; where the networked device is further configured to determine that a user input has not been received for a threshold amount of time, and in response to the determination that the user input has not been received for the threshold amount of time, determine the first current time associated with the internal clock; where the networked device is further configured to calculate the first metric index value based on a modulo operation including the screen change time interval and a number of metrics included in the indication of the one or more metrics to be displayed; where the networked device is further configured to determine the second current time before an amount of time equal to the screen change time interval has elapsed since the first time; where the networked device is further configured to determine the second current time at a time that precedes the second time by a predefined amount of time; where the networked device is further configured to, within the screen change time interval from the second time, determine a third current time associated with the internal clock, calculate a third metric index value different from the second metric index value based on the third current time, and replace the second delivery metric displayed on the display with a third metric associated with the third metric index value at a third time that is not later than the second time by the time period equal to the screen change time interval, such that a first time difference between the first time and the second time is shorter than a second time difference between the second time and the third time; and where the second time difference is equal to the screen change time interval, and the first time difference is shorter than the screen change time interval.

One aspect of the disclosure provides a system adapted to provide synchronized screen content. The system may include a server and a plurality of infusion pumps configured to deliver medications to one or more patients and in network communication with the server. Each respective infusion pump of the plurality of infusion pumps networked devices may include (i) a display configured to display one or more metrics of a plurality of metrics maintained by the respective infusion pump and (ii) a memory configured to store internal clock data usable to determine a current time associated with the respective networked device. The respective infusion pump is configured to: receive a clock synchronization data from the server, wherein the clock synchronization data is indicative of a reference time associated with the server; update the internal clock data based on the clock synchronization data; receive metric display data from the server, wherein the metric display data comprises a metric display period and an indication of two or more metrics to be displayed on the display of the respective networked device; based on a determination that a user input has not been received for a threshold amount of time, determine a first current time associated with the internal clock data; calculate a first metric index based on the first current time, the metric display period, and the indication of the two or more metrics received from the server; determine a first metric of the plurality of metrics that is associated with the first metric index; cause the first metric to be displayed on the display of the respective infusion pump at a first time; within at least the metric display period from the first time, determine a second current time associated with the internal clock data; calculate a second metric index based on the second current time, the metric display period, and the indication of the two or more metrics received from the server; determine a second metric of the plurality of metrics that is associated with the second metric index; and cause the first metric displayed on the display of the respective infusion pump to be replaced with the second metric at a second time that is not later than the first time by a time period equal to the metric display period.

The system can further include any sub-combination of one or more of the following features: where the respective infusion pump is further configured to calculate the first metric index value based on a modulo operation comprising a length of the metric display period and a count of the two or more metrics included in the indication received from the server; and where the respective infusion pump is further configured to, within the metric display period from the second time, determine a third current time associated with the internal clock data, calculate a third metric index based on the third current time, the metric display period, and the indication of the two or more metrics received from the server, determine a third metric of the plurality of metrics that is associated with the third metric index, and cause the second metric displayed on the display of the respective infusion pump to be replaced with the third metric at a third time that is not later than the second time by the time period equal to the metric display period, where a first time difference between the first time and the second time is shorter than a second time difference between the second time and the third time.

One aspect of the disclosure provides an apparatus adapted to provide synchronized screen content. The apparatus may include a display, a processor in communication with the display, and a memory storing an internal clock data according to which one or more metrics are to be displayed on the display. The memory may further store instructions that, when executed by the processor, configure the processor to: determine a first current time based on the internal clock data; identify a first one of a plurality of screen contents to be displayed on the display based on (i) the first current time, (ii) a content display period length indicative of a duration for which the first screen content is to be displayed on the display, and (iii) a screen content count indicative of a count of the plurality of screen contents to be displayed on the display; and cause the first screen content to be displayed on the display at a first time for a first duration that is less than or equal to the content display period length.

The apparatus can further include any sub-combination of one or more of the following features: where the instructions, when executed by the processor, further configure the processor to determine that a user input has not been received for a threshold amount of time, in response to the determination that the user input has not been received for the threshold amount of time, determine the first current time based on the internal clock data; where the instructions, when executed by the processor, further configure the processor to calculate a screen content index based on the first current time and the content display period length, and identify the first screen content based on the calculated screen content index; where the instructions, when executed by the processor, further configure the processor to calculate the screen content index based on a modulo operation comprising the content display period length and the screen content count; where the instructions, when executed by the processor, further configure the processor to determine a second current time before an amount of time equal to the content display period length has elapsed since the first time, identify a second one of the plurality of screen contents based on (i) the second current time, (ii) the content display period length, and (iii) the screen content count, cause the second screen content to be displayed on the display at a second time for a second duration that is equal to the content display period length; where the instructions, when executed by the processor, further configure the processor to cause the first screen content and the second screen content to be displayed on the display such that the first duration for which the first screen content is displayed on the display is shorter than the second duration for which the second screen content is displayed on the display; where the instructions, when executed by the processor, further configure the processor to determine the second current time at a time that precedes the second time by a predefined amount of time; where the instructions, when executed by the processor, further configure the processor to receive a clock synchronization data from a server in network communication with the apparatus, and update the internal clock data based on the clock synchronization data; where the instructions, when executed by the processor, further configure the processor to transmit a clock synchronization request to the server according to a predefined schedule.

One aspect of the disclosure provides a method of providing synchronized screen content. The method may include: determining a first current time associated with a medical device based on an internal clock associated with the medical device; identifying a first one of a plurality of screen contents to be displayed on a display of the medical device based on (i) the first current time, (ii) a content display period length indicative of a duration for which the identified screen content is to be displayed on the display, and (iii) a screen content count indicative of a count of the plurality of screen contents to be displayed on the display; and displaying the identified screen content on the display at a first time for a duration that is less than or equal to the content display period length.

The method can further include any sub-combination of one or more of the following features: where the method further includes determining that a user input has not been received for a threshold amount of time, and in response to determining that the user input has not been received for the threshold amount of time, determining the first current time based on the internal clock data; where the method further includes calculating a screen content index based on the first current time and the content display period length, and identifying the first screen content based on the calculated screen content index; where the method further includes calculating the screen content index based on a modulo operation comprising the content display period length and the screen content count; where the method further includes determining a second current time before an amount of time equal to the content display period length has elapsed since the first time, identifying a second one of the plurality of screen contents based on (i) the second current time, (ii) the content display period length, and (iii) the screen content count, displaying the second screen content on the display at a second time for a second duration that is equal to the content display period length; where the method further includes displaying the first screen content and the second screen content such that the first duration for which the first screen content is displayed is shorter than the second duration for which the second screen content is displayed; where the method further includes receiving a clock synchronization data from a server in network communication with the medical device, and updating the internal clock data based on the clock synchronization data; where the method further includes transmitting a clock synchronization request to the server according to a predefined schedule.

ADDITIONAL EXAMPLE EMBODIMENTS
(EEs)

EE 1. A system configured to provide synchronized screen content, the system comprising: a server; and a plurality of infusion pumps configured to deliver medications to one or more patients and in network communication with the server, wherein each respective infusion pump of the plurality of infusion pumps comprises (i) a display configured to display one or more metrics of a plurality of metrics maintained by the respective infusion pump and (ii) a memory configured to store internal clock data usable to determine a current time associated with the respective networked device, wherein the respective infusion pump is configured to: receive a clock synchronization data from the server, wherein the clock synchronization data is indicative of a reference time associated with the server; update the internal clock data based on the clock synchronization data; receive metric display data from the server, wherein the metric display data comprises a metric display period and an indication of two or more metrics to be displayed on the display of the respective networked device; based on a determination that a user input has not been received for a threshold amount of time, determine a first current time associated with the internal clock data; calculate a first metric index based on the first current time, the metric display period, and the indication of the two or more metrics received from the server; determine a first metric of the plurality of metrics that is associated with the first metric index; cause the first metric to be displayed on the display of the respective infusion pump at a first time; within at least the metric display period from the first time, determine a second current time associated with the internal clock data; calculate a second metric index based on the second current time, the metric display period, and the indication of the two or more metrics received from the server; determine a second metric of the plurality of metrics that is associated with the second metric index; and cause the first metric displayed on the display of the respective infusion pump to be replaced with the second metric at a second time that is not later than the first time by a time period equal to the metric display period.

EE 2. The system of EE 1, wherein the respective infusion pump is further configured to calculate the first metric index value based on a modulo operation comprising a length of the metric display period and a count of the two or more metrics included in the indication received from the server.

EE 3. The system of EE 1, wherein the respective infusion pump is further configured to: within the metric display period from the second time, determine a third current time associated with the internal clock data; calculate a third metric index based on the third current time, the metric display period, and the indication of the two or more metrics received from the server; determine a third metric of the plurality of metrics that is associated with the third metric index; and cause the second metric displayed on the display of the respective infusion pump to be replaced with the third metric at a third time that is not later than the second time by the time period equal to the metric display period, wherein a first time difference between the first time and the second time is shorter than a second time difference between the second time and the third time.

EE 4. An apparatus configured to provide synchronized screen content of at least one medical device, the apparatus comprising: a display; a processor in communication with the display; a memory storing an internal clock data according to which one or more metrics are to be displayed on the display, the memory further storing instructions that, when executed by the processor, configure the processor to: determine a first current time based on the internal clock data; identify a first one of a plurality of medical device screen contents to be displayed on the display based on (i) the first current time, (ii) a content display period length indicative of a duration for which the first medical device screen content is to be displayed on the display, and (iii) a screen content count indicative of a count of the plurality of medical device screen contents to be displayed on the display; and cause the first medical device screen content to be displayed on the display at a first time for a first duration that is less than or equal to the content display period length.

EE 5. The apparatus of EE 4, wherein the instructions, when executed by the processor, further configure the processor to: determine that a user input has not been received for a threshold amount of time; and in response to the determination that the user input has not been received for the threshold amount of time, determine the first current time based on the internal clock data.

EE 6. The apparatus of EE 4, wherein the instructions, when executed by the processor, further configure the processor to: calculate a screen content index based on the first current time and the content display period length; and identify the first medical device screen content based on the calculated screen content index.

EE 7. The apparatus of EE 6, wherein the instructions, when executed by the processor, further configure the processor to calculate the screen content index based on a modulo operation comprising the content display period length and the screen content count.

EE 8. The apparatus of EE 4, wherein the instructions, when executed by the processor, further configure the processor to: determine a second current time before an amount of time equal to the content display period length has elapsed since the first time; identify a second one of the plurality of medical device screen contents based on (i) the second current time, (ii) the content display period length, and (iii) the screen content count; and cause the second medical device screen content to be displayed on the display at a second time for a second duration that is equal to the content display period length.

EE 9. The apparatus of EE 8, wherein the instructions, when executed by the processor, further configure the processor to cause the first medical device screen content and the second medical device screen content to be displayed on the display such that the first duration for which the first medical device screen content is displayed on the display is shorter than the second duration for which the second medical device screen content is displayed on the display.

EE 10. The apparatus of EE 8, wherein the instructions, when executed by the processor, further configure the processor to determine the second current time at a time that precedes the second time by a predefined amount of time.

EE 11. The apparatus of EE 4, wherein the instructions, when executed by the processor, further configure the processor to: receive a clock synchronization data from a server in network communication with the apparatus; and update the internal clock data based on the clock synchronization data.

EE 12. The apparatus of EE 11, wherein the instructions, when executed by the processor, further configure the processor to transmit a clock synchronization request to the server according to a predefined schedule.

EE 13. A method of providing synchronized screen content of at least one medical device, the method comprising: determining a first current time associated with a medical device based on an internal clock associated with the medical device; identifying a first one of a plurality of medical device screen contents to be displayed on a display of the medical device based on (i) the first current time, (ii) a content display period length indicative of a duration for which the identified medical device screen content is to be displayed on the display, and (iii) a screen content count indicative of a count of the plurality of medical device screen contents to be displayed on the display; and displaying the identified medical device screen content on the display at a first time for a duration that is less than or equal to the content display period length.

EE 14. The method of EE 13, further comprising: determining that a user input has not been received for a threshold amount of time; and in response to determining that the user input has not been received for the threshold amount of time, determining the first current time based on the internal clock data.

EE 15. The method of EE 13, further comprising: calculating a screen content index based on the first current time and the content display period length; and identifying the first medical device screen content based on the calculated screen content index.

EE 16. The method of EE 15, further comprising calculating the screen content index based on a modulo operation comprising the content display period length and the screen content count.

EE 17. The method of EE 13, further comprising: determining a second current time before an amount of time equal to the content display period length has elapsed since the first time; identifying a second one of the plurality of medical device screen contents based on (i) the second current time, (ii) the content display period length, and (iii) the screen content count; and displaying the second medical device screen content on the display at a second time for a second duration that is equal to the content display period length.

EE 18. The method of EE 17, further comprising displaying the first medical device screen content and the second medical device screen content such that the first duration for which the first medical device screen content is displayed is shorter than the second duration for which the second medical device screen content is displayed.

EE 19. The method of EE 13, further comprising: receiving a clock synchronization data from a server in network communication with the medical device; and updating the internal clock data based on the clock synchronization data.

EE 20. The method of EE 19, further comprising transmitting a clock synchronization request to the server according to a predefined schedule.

OTHER CONSIDERATIONS

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. An apparatus comprising:
one or more processors; and
one or more memories storing instructions that, when executed by the one or more processors, configure the one or more processors to:
determine a current time;
determine a display period length associated with at least one displayable metric;
determine, based at least in part on the current time and the display period length, a first metric to be displayed;
cause the first metric to be displayed on a display; and
before the first metric is displayed for the display period length, cause the display to transition from displaying the first metric to displaying a second metric that is different from the first metric.

2. The apparatus of claim 1, wherein the first metric is one of dose, rate, volume infused, volume to be infused, or time remaining, and the second metric is another one of dose, rate, volume infused, volume to be infused, or time remaining.

3. The apparatus of claim 1, wherein the instructions, when executed by the one or more processors, further configure the one or more processors to determine the current time in response to a determination that the apparatus has not received a user input for at least a threshold amount of time.

4. The apparatus of claim 1, wherein the instructions, when executed by the one or more processors, further configure the one or more processors to cause an internal clock of the apparatus to be synchronized based at least in part on a signal received from a server in networked communication with the apparatus.

5. The apparatus of claim 1, wherein the instructions, when executed by the one or more processors, further configure the one or more processors to cause an internal clock of the apparatus to be synchronized based at least in part on a signal received from an atomic clock.

6. The apparatus of claim 1, wherein the instructions, when executed by the one or more processors, further configure the one or more processors to, after the second metric is displayed for at least a duration indicated by the display period length, cause the display to transition from displaying the second metric to displaying a third metric that is different from the first metric and the second metric.

7. The apparatus of claim 1, wherein the instructions, when executed by the one or more processors, further configure the one or more processors to cause the first metric to be displayed (i) in a specific size, (ii) in a specific color, or (iii) along with a specific indicator, wherein the specific size, the specific color, or the specific indicator provides additional information other than that indicated by a displayed value of the first metric.

8. A method comprising:
determining a current time associated with a networked device;
determining a display period length associated with at least one displayable metric;
determining, based at least in part on the current time and the display period length, a first metric to be displayed;
displaying the first metric on a display; and
before the first metric is displayed for the display period length, causing the display to transition from displaying the first metric to displaying a second metric that is different from the first metric.

9. The method of claim 8, wherein the first metric is one of dose, rate, volume infused, volume to be infused, or time remaining, and the second metric is another one of dose, rate, volume infused, volume to be infused, or time remaining.

10. The method of claim 8, further comprising determining the current time in response to determining that the networked device has not received a user input for at least a threshold amount of time.

11. The method of claim 8, further comprising synchronizing a clock based at least in part on a signal received from a server in networked communication with the networked device.

12. The method of claim 8, wherein the networked device is in networked communication with a server, the method further comprising synchronizing a clock based at least in part on a signal received from other than the server.

13. The method of claim 8, further comprising, after the second metric is displayed for at least a duration indicated by the display period length, transitioning from displaying the second metric on the display to displaying a third metric on the display, wherein the third metric is different from the first metric and the second metric.

14. The method of claim 8, further comprising displaying the first metric (i) in a specific size, (ii) in a specific color, or (iii) along with a specific indicator, wherein the specific size, the specific color, or the specific indicator provides additional information other than that indicated by a displayed value of the first metric.

15. A system comprising:
a server; and
a plurality of networked devices in networked communication with the server, wherein a first networked device of the plurality of networked devices is configured to at least:
determine a current time;
determine a display period length associated with at least one displayable metric;
determine, based at least in part on the current time and the display period length, a first metric to be displayed;
cause the first metric to be displayed on a display; and
before the first metric is displayed for the display period length, cause the display to transition from displaying the first metric to displaying a second metric that is different from the first metric.

16. The system of claim 15, wherein the first networked device is further configured to determine the current time in response to a determination that the first networked device has not received a user input for at least a threshold amount of time.

17. The system of claim 15, wherein the server is configured to transmit a set of infusion pump settings or delivery parameters to the first networked device, the first networked device further configured to cause a clock to be synchronized based at least in part on a signal received from the server.

18. The system of claim 15, wherein the server is configured to transmit a set of infusion pump settings or delivery parameters to the first networked device, the first networked device further configured to cause a clock to be synchronized based at least in part on a signal received from other than the server.

19. The system of claim 15, wherein the first networked device is further configured to, after the second metric is displayed for at least a duration indicated by the display period length, cause the display to transition from displaying the second metric to displaying a third metric that is different from the first metric and the second metric.

20. The system of claim 15, wherein the first networked device is further configured to cause the first metric to be displayed (i) in a specific size, (ii) in a specific color, or (iii) along with a specific indicator, wherein the specific size, the specific color, or the specific indicator provides additional information other than that indicated by a displayed value of the first metric.

* * * * *